(12) United States Patent
Penner et al.

(10) Patent No.: US 11,913,929 B2
(45) Date of Patent: Feb. 27, 2024

(54) NANOWIRE BASED HYDROGEN SENSORS

(71) Applicant: THE REGENTS OF THE UNIVERSITY OF CALIFORNIA, Oakland, CA (US)

(72) Inventors: Reginald M. Penner, Newport Beach, CA (US); Won-Tae Koo, Daejeon (KR); Il-Doo Kim, Daejeon (KR)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 196 days.

(21) Appl. No.: 16/791,159

(22) Filed: Feb. 14, 2020

(65) Prior Publication Data
US 2020/0256838 A1    Aug. 13, 2020

Related U.S. Application Data

(63) Continuation of application No. PCT/US2018/046759, filed on Aug. 14, 2018.

(60) Provisional application No. 62/545,329, filed on Aug. 14, 2017.

(51) Int. Cl.
| | |
|---|---|
| *G01N 33/00* | (2006.01) |
| *C23C 14/58* | (2006.01) |
| *C25D 1/04* | (2006.01) |
| *C25D 3/50* | (2006.01) |
| *C25D 5/02* | (2006.01) |
| *C25D 5/40* | (2006.01) |

(Continued)

(52) U.S. Cl.
CPC ....... *G01N 33/005* (2013.01); *C23C 14/5873* (2013.01); *C25D 1/04* (2013.01); *C25D 3/50* (2013.01); *C25D 5/022* (2013.01); *C25D 5/40* (2013.01); *C25D 5/48* (2013.01); *G01N 27/127* (2013.01)

(58) Field of Classification Search
CPC .................................................. G01N 33/005
See application file for complete search history.

(56) References Cited

U.S. PATENT DOCUMENTS

| | | | |
|---|---|---|---|
| 2009/0197209 A1 | 8/2009 | Penner et al. | |
| 2012/0085145 A1* | 4/2012 | Xiao | B82Y 30/00 428/401 |
| 2017/0003272 A1* | 1/2017 | Kim | B01J 35/0033 |

(Continued)

FOREIGN PATENT DOCUMENTS

| | | | | |
|---|---|---|---|---|
| CN | 102731538 B | * 12/2015 | | B82Y 30/00 |
| WO | WO 2014/098583 A1 | 6/2014 | | |
| WO | WO-2014098583 A1 | * 6/2014 | | G01N 21/7703 |

OTHER PUBLICATIONS

Zhang et al., "Nanowire-directed templating synthesis of metal-organic framework nanofibers and their derived porous doped carbon nanofibers for enhanced electrocatalysis", JACS, 2014, 136, 14385-14388. (Year: 2014).*

(Continued)

*Primary Examiner* — Kristina M Deherrera
*Assistant Examiner* — Fatemeh Esfandiari Nia
(74) *Attorney, Agent, or Firm* — ONE LLP

(57) ABSTRACT

Systems and methods using engineered nanofiltration layers to facilitate acceleration of palladium nanowire hydrogen sensors. The sensors include a metal-organic framework (MOF) assembled on palladium (Pd) nanowires (NWs) for highly selective and ultra-fast H2 molecule detection.

8 Claims, 15 Drawing Sheets

(51) Int. Cl.
    *C25D 5/48*    (2006.01)
    *G01N 27/12*   (2006.01)

(56) References Cited

U.S. PATENT DOCUMENTS

2017/0198393 A1* 7/2017 Stassen ............... C23C 16/4408
2018/0011010 A1  1/2018 Chang et al.

OTHER PUBLICATIONS

Lu, Guang, et al. "Engineering ZIF-8 Thin Films for Hybrid MOF-Based Devices." Advanced Materials 24.29 (2012): 3970-3974 (Year: 2012).*

Yang, Fan, David K. Taggart, and Reginald M. Penner. "Joule heating a palladium nanowire sensor for accelerated response and recovery to hydrogen gas." small 6.13 (2010): 1422-1429 (Year: 2010).*

Yang, Fan, et al. "The surface scattering-based detection of hydrogen in air using a platinum nanowire." Nano letters 12.6 (2012): 2924-2930 (Year: 2012).*

Drobek, Martin, et al. "MOF-based membrane encapsulated ZnO nanowires for enhanced gas sensor selectivity." ACS applied materials & interfaces 8.13 (2016): 8323-8328 (Year: 2016).*

CN-102731538-B-English (Year: 2015).*

Lin, Lu, et al. "In situ fabrication of a perfect Pd/ZnO@ ZIF-8 core-shell microsphere as an efficient catalyst by a ZnO support-induced ZIF-8 growth strategy." Nanoscale 7.17 (2015): 7615-7623.) (Year: 2015).*

WO, PCT/US18/46759 ISR and Written Opinion, dated Oct. 24, 2018.

Lu, G., et al., "Engineering ZIF-8 Thin Films for Hybrid MOF-based Devices", Advanced Materials, 2012, vol. 24, No. 29, pp. 3970-3974.

* cited by examiner

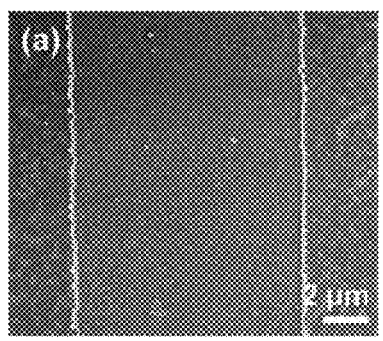 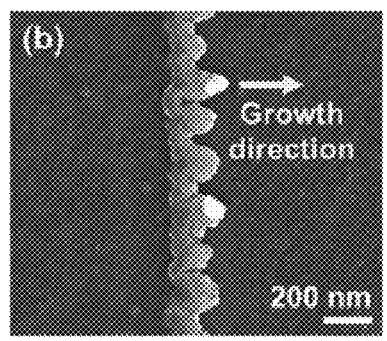 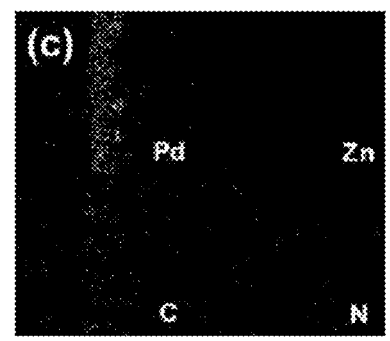
FIG. 2A  FIG. 2B  FIG. 2C
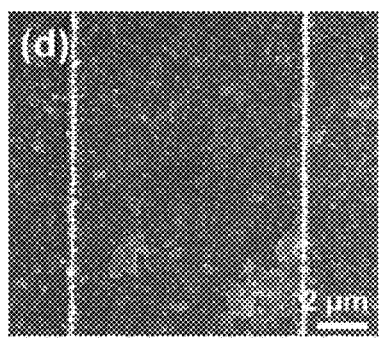 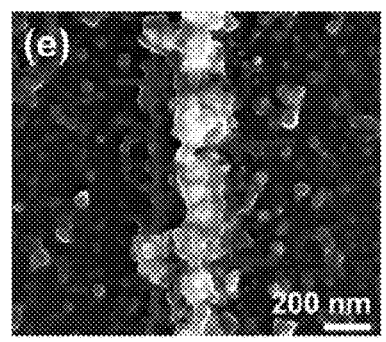 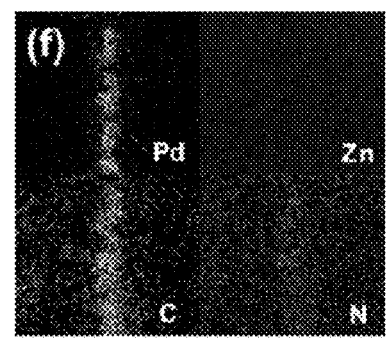
FIG. 2D  FIG. 2E  FIG. 2F
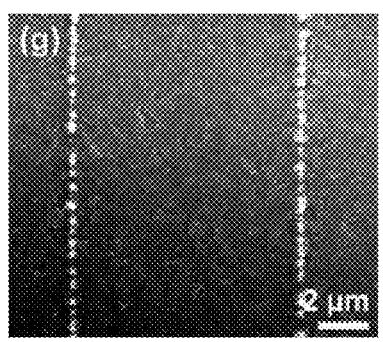 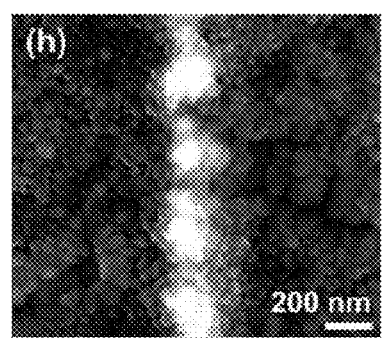 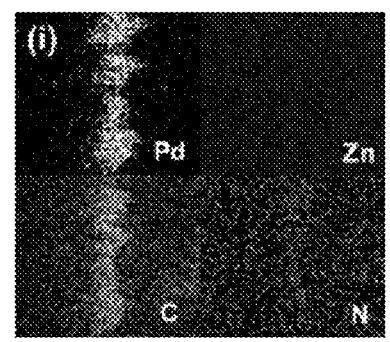
FIG. 2G  FIG. 2H  FIG. 2I
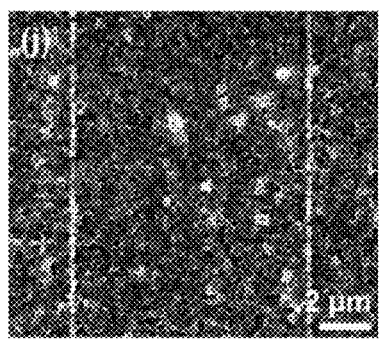 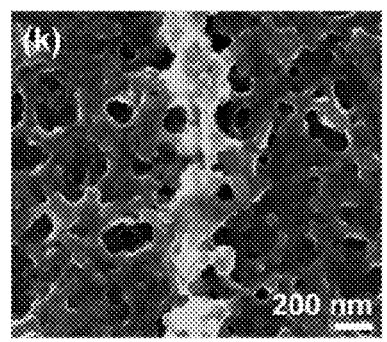 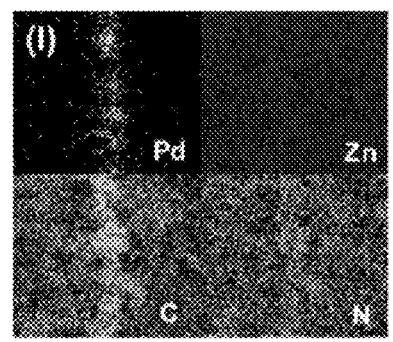
FIG. 2J  FIG. 2K  FIG. 2L

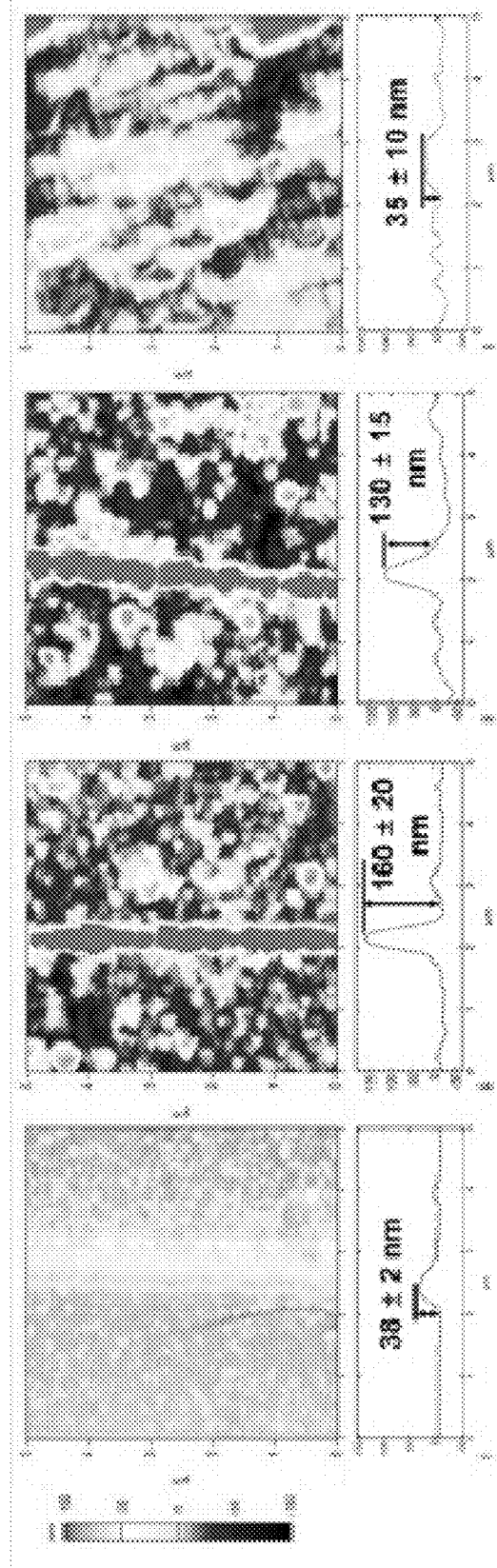
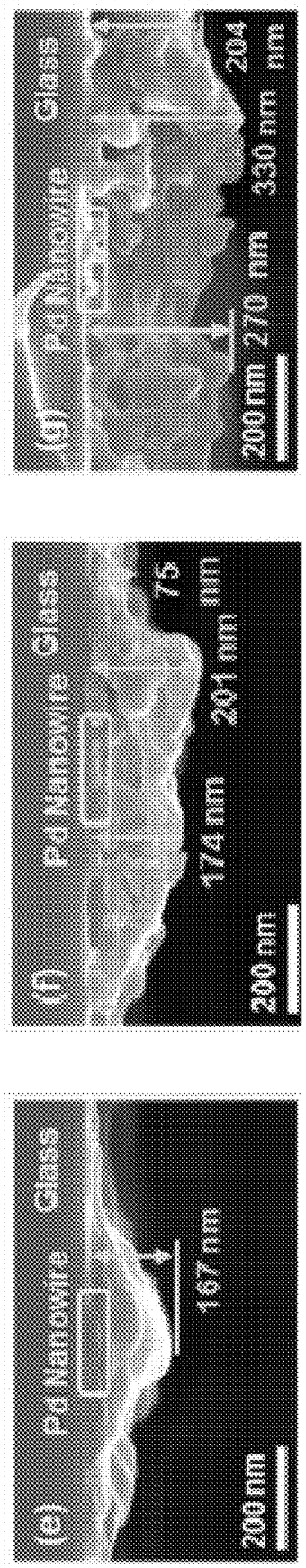
FIG. 9A  FIG. 9B  FIG. 9C  FIG. 9D
FIG. 9E  FIG. 9F  FIG. 9G

NANOWIRE BASED HYDROGEN SENSORS

CROSS-REFERENCE TO RELATED APPLICATIONS

The subject application is a continuation of PCT Patent Application No. PCT/US18/46759, filed Aug. 14, 2018, which claims priority to U.S. Provisional Patent Application No. 62/545,329, filed on Aug. 14, 2017, both of which are incorporated by reference herein in their entireties for all purposes.

FIELD

The subject matter described herein relates generally to nanowire based hydrogen sensors and, more particularly, to systems and methods using engineered nanofiltration layers to facilitate acceleration of palladium nanowire hydrogen sensors.

BACKGROUND

Hydrogen has been regarded as a next-generation energy source due to its abundance in nature and high efficiency in energy combustion. In particular, the combustion reaction of hydrogen produces only water ($H_2O$) as a by-product, thus hydrogen based energy systems have attracted much attention as clean energy sources. However, hydrogen easily reacts with oxygen molecules in air, which substantially causes a risk of flammability. In addition, since hydrogen is colorless, odorless, and tasteless, it is difficult to detect hydrogen leakage. Moreover, hydrogen diffuses quickly in air due to its small size and the fact that it is lightweight. Therefore, the development of high performance hydrogen gas sensors with fast response and recovery time is necessary.

SUMMARY

The various embodiments provided herein are generally directed to systems and methods using engineered nanofiltration layers to facilitate acceleration of palladium (Pd) nanowire (NW) hydrogen ($H_2$) sensors. The various embodiments provided herein include a metal-organic framework (MOF) assembled on palladium (Pd) nanowires (NWs) for highly selective and ultra-fast $H_2$ molecule detection. Palladium (Pd) metal is a representative $H_2$ sensing material, but its $H_2$ sensing properties are easily degraded by $O_2$ in air. In the present embodiments, as a protective $H_2$ filter-layer, polyhedron particles of Zn based zeolite imidazole framework (ZIF-8) are directly assembled on lithographically patterned Pd NWs, leading to the creation of ZIF-8/Pd NWs bi-layered sensors. The ZIF-8 filter has many micropores (0.34 nm for gas diffusion) which allows for the predominant penetration of hydrogen molecules with a kinetic diameter of 0.289 nm, while relatively larger gas molecules including oxygen (0.345 nm) and nitrogen (0.364 nm), in air, are effectively screened, resulting in superior hydrogen sensing properties. The present Pd NWs filtered by the ZIF-8 membrane (Pd NWs@ZIF-8) exhibited significantly improved $H_2$ responsiveness (7 sec to 1% of $H_2$) and recovery speed (10 sec to 1% of $H_2$) to low concentration ranges of hydrogen at room temperature in air, compared to pristine Pd NWs (164 sec for response and 229 sec for recovery to 1% of $H_2$). Although the hydrogen response (3.47% to 1% of $H_2$) of Pd NWs@ZIF-8 was slightly decreased when compared with pure Pd NWs (5.88% to 1% of $H_2$), the Pd NWs@ZIF-8 showed 20-fold faster recovery and response speed than pristine Pd NWs. These results can be attributed, in part, to the molecular sieving and acceleration effect of ZIF-8 covered on Pd NWs. These results also rank highest among currently known room temperature Pd based $H_2$ sensors.

Other systems, methods, features and advantages of the example embodiments will be or will become apparent to one with skill in the art upon examination of the following figures and detailed description.

BRIEF DESCRIPTION OF DRAWINGS

The details of the example embodiments, including structure and operation, may be gleaned in part by study of the accompanying figures, in which like reference numerals refer to like parts. The components in the figures are not necessarily to scale, emphasis instead being placed upon illustrating the principles of the disclosure. Moreover, all illustrations are intended to convey concepts, where relative sizes, shapes and other detailed attributes may be illustrated schematically rather than literally or precisely.

FIG. 2A illustrates a low magnification SEM image of exemplary samples patterned with Pd NWs.

FIG. 2B illustrates a high magnification SEM image of exemplary samples patterned with Pd NWs.

FIG. 2C illustrates an EDS elemental mapping image of exemplary samples patterned with Pd NWs.

FIG. 2D illustrates a low magnification SEM image of exemplary Pd NWs@ZIF-8_2 h according to embodiments of the present disclosure.

FIG. 2E illustrates a high magnification SEM image of exemplary Pd NWs@ZIF-8_2 h according to embodiments of the present disclosure.

FIG. 2F illustrates an EDS elemental mapping image of exemplary Pd NWs@ZIF-8_2 h according to embodiments of the present disclosure.

FIG. 2G illustrates a low magnification SEM image of exemplary Pd NWs@ZIF-8_4 h according to embodiments of the present disclosure.

FIG. 2H illustrates a high magnification SEM image of exemplary Pd NWs@ZIF-8_4 h according to embodiments of the present disclosure.

FIG. 2I illustrates an EDS elemental mapping image of exemplary Pd NWs@ZIF-8_4 h according to embodiments of the present disclosure.

FIG. 2J illustrates a low magnification SEM image of exemplary Pd NWs@ZIF-8_6 h according to embodiments of the present disclosure.

FIG. 2K illustrates a high magnification SEM image of exemplary Pd NWs@ZIF-8_6 h according to embodiments of the present disclosure.

FIG. 2L illustrates an EDS elemental mapping image of exemplary Pd NWs@ZIF-8_6 h according to embodiments of the present disclosure.

FIG. 9A illustrates AFM and depth profiles of exemplary Pd NWs.

FIG. 9B illustrates AFM and depth profiles of exemplary Pd NWs@ZIF-8_2h, according to embodiments of the present disclosure.

FIG. 9C illustrates AFM and depth profiles of exemplary Pd NWs@ZIF-8_4h, according to embodiments of the present disclosure FIG. 9D illustrates AFM and depth profiles of exemplary Pd NWs@ZIF-8_6h, according to embodiments of the present disclosure FIG. 9E illustrates a cross-sectional SEM image of exemplary Pd NWs@ZIF-8_2h, according to embodiments of the present disclosure FIG. 9F illustrates a cross-sectional SEM image of exemplary Pd NWs@ZIF-8_4h, according to embodiments of the present disclosure FIG. 9G illustrates a cross-sectional SEM image of exemplary Pd NWs@ZIF-8_6h, according to embodiments of the present disclosure

It should be noted that elements of similar structures or functions are generally represented by like reference numerals for illustrative purpose throughout the figures. It should also be noted that the figures are only intended to facilitate the description of the preferred embodiments.

DETAILED DESCRIPTION

Figure 1:
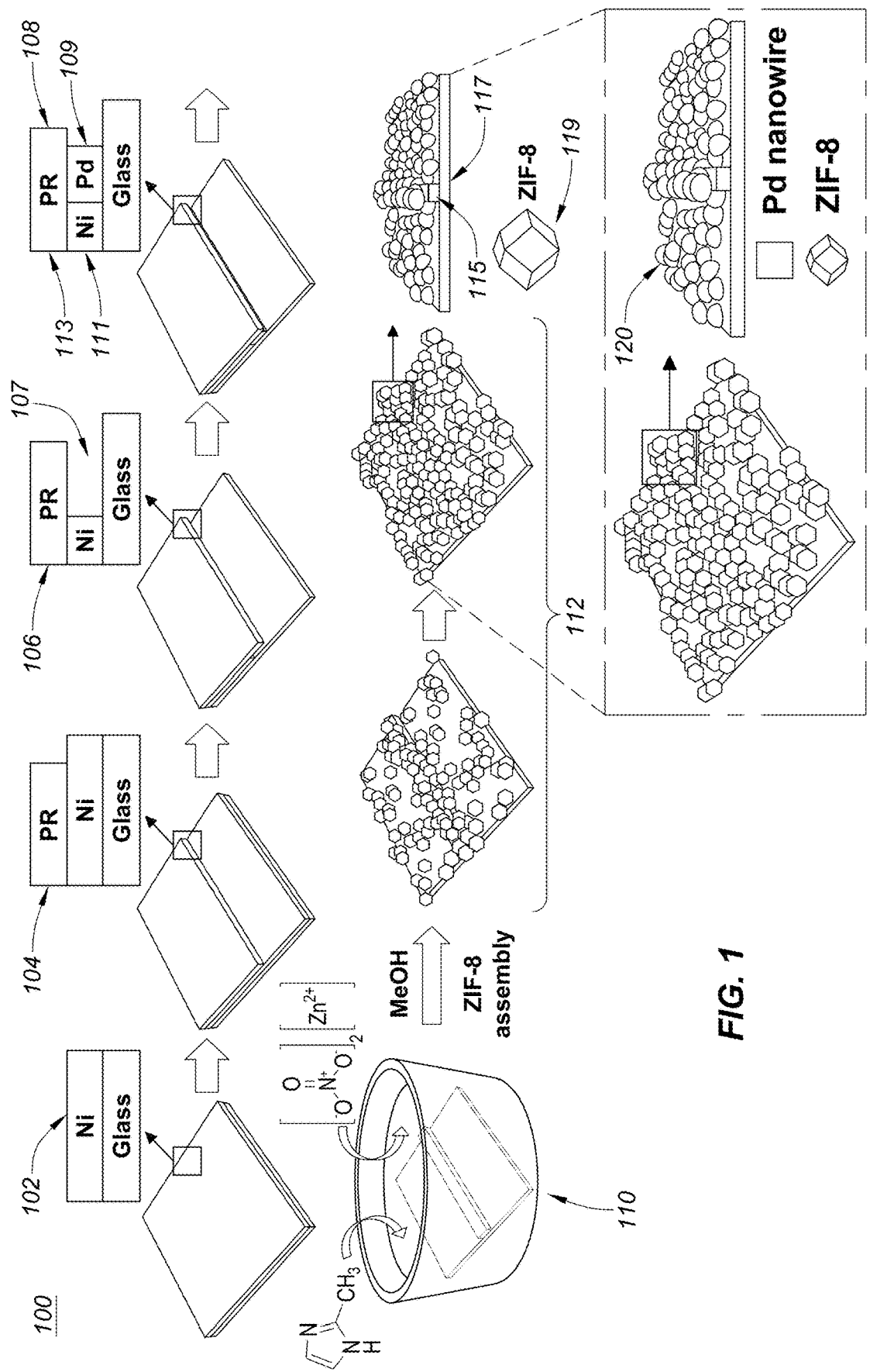
FIG. 1 shows a schematic illustration of an exemplary synthesis process of an exemplary Pd NWs@ZIF-8, according to embodiments of the present disclosure.

Each of the additional features and teachings disclosed below can be utilized separately or in conjunction with other features and teachings to provide ultra-fast responding and recovering palladium nanowire based hydrogen sensors. Representative examples of the embodiments described herein, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

Among the various types of hydrogen gas sensors, palladium (Pd) based resistor-type hydrogen sensors have been widely studied due to their simple operation principle and reasonably successful $H_2$ sensing properties. Since the reaction of Pd with hydrogen induces the increase of the Pd base-resistance by forming $PdH_x$, hydrogen can be easily detected by monitoring the resistance variation of Pd, even at room temperature (RT). So far, a number of Pd based hydrogen sensors, including Pd nanowires (NWs), Pd nanotubes, Pd films, and Pd NW networks, have been suggested. However, in most cases, the hydrogen sensing properties of these sensors have been evaluated in nitrogen ($N_2$) atmospheres, not in air. Since there are a number of gas species in air, the sensing properties of Pd can be significantly deteriorated by the existence of interfering gases, such as oxygen ($O_2$), sulfur dioixde ($SO_2$), hydrogen sulfide ($H_2S$), and so on. For instance, oxygen molecules (about 21% in air) react with adsorbed hydrogen on the surface of Pd by the following equations (reaction 1 and 2).

$$2H_2(ads)+O_2(gas) \rightarrow 2H_2O(gas) \quad (1)$$

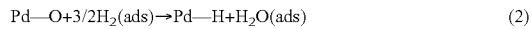
$$Pd-O+3/2H_2(ads) \rightarrow Pd-H+H_2O(ads) \quad (2)$$

These reactions lead to a significant decrease in the number of adsorbed hydrogen molecules. Moreover, oxygen species adsorbed on Pd layers hinder the surface reaction sites for hydrogen adsorption. For these reasons, poor hydrogen sensing responses and sluggish reaction kinetics are often observed in Pd-based sensors, particularly when used for measurements in an air environment. The functionalization of Pt catalysts on Pd NWs has been proposed to minimize the screening effect of $O_2$ on Pd NW-based sensors. Since Pt catalysts can effectively reduce oxygen reaction on Pd NWs by the reaction of oxygen and Pt, enhanced hydrogen detection performance was observed. However, for the activation of Pt catalysts, the sensors were operated at high temperatures (100° C.), leading to the degradation of response and detection limits of the sensors.

Metal-organic frameworks (MOFs) consisting of metal node and organic linkers have been rapidly emerged in various fields, such as catalysis, gas separation, gas sensor, and drug delivery, and so on, due to its incredibly high surface area, ultra-high porosity, and tunable structures. Among the various types of MOFs, zinc (Zn) based zeolite imidazole framework (ZIF-8) has been widely studied due to its facile synthesis by simple precipitation reaction in solvents, such as water or methanol, and high stability. In particular, ZIF-8 has high hydrogen permeability due to its microporous cavity structure. The ultra-small size (0.34 nm) of ZIF-8 micropores allows selective penetration of hydrogen (0.289 nm) molecules into an inner cavity, while larger gas molecules are mostly screened. Recently, ZIF-8 was used as a protection layer for selective $H_2$ sensing of ZnO based sensing materials. Since Zn sources on the surface of ZnO serve a seed layer for the growth of ZIF-8, ZIF-8 can be easily grown on the ZnO. The ZnO surrounded by ZIF-8 membrane showed improved hydrogen sensing properties. Although semiconducting metal-oxide (SMO) sensors have been successfully commercialized, their operation temperature is relatively high (250-400° C.) and high humidity dependence hampers the reliability of SMO sensors, particularly in operation at RT. To satisfy the hydrogen sensing performances (response time <60 sec at $H_2$ 1% and recovery time <60 sec) defined by The U.S. Department of Energy (DOE), rationally designed hydrogen sensors with fast reaction speed are needed. Due to the generally accepted expectation that the use of nanofiltration devices would impose a tortuous barrier to gases in front of the transducer, thereby slowing response and recovery speeds for the sensors, the use of nanofiltration devices has not previously been explored. The present results illustrate that exactly the opposite is true: $H_2$ sensor response and recovery are both dramatically accelerated.

The terms "response" and "response time" and related terms refer to a time interval between the time when an instantaneous variation in volume ratio is produced at a sensor inlet and the time when the response reaches a stated percentage of final indication. A final indication may be, in some embodiments, an indication given by a sensor after stabilization.

The terms "recovery" and "recovery time" and related terms refer to a time interval required for a sensor to return to a percentage (e.g, 90%) of a normal baseline upon removal of the target gas (e.g., Hydrogen).

It will be appreciated that the use of the term "hydrogen" throughout the present disclosure is used interchangeably with the term "$H_2$."

Embodiments of the present disclosure provide bi-layered hydrogen sensors, i.e., lithographically patterned Pd NWs filtered by ZIF-8 as a molecular sieving layer (Pd NWs@ZIF-8), which have remarkably high $H_2$ detection rate. Patterned Pd NWs prepared by the lithographically patterned NW deposition (LPNE) process, as a current state-of-art technology for hydrogen gas sensors, have offered high sensing properties for the detection of hydrogen. However, it is still urgent to develop Pd-based fast-responding/recovery $H_2$ sensors to be operated in air. To overcome the inherent limitation of Pd-based $H_2$ sensors, in the present embodiments, ZIF-8 is assembled on Pd NWs as a protection layer that can facilitate the adsorption and desorption of hydrogen. The present embodiments include fast growth of ZIF-8 on Pd NWs by heterogeneous nucleation.

The various embodiments provided herein are generally directed to systems and methods using engineered nanofiltration layers to facilitate acceleration of palladium (Pd) nanowire (NW) hydrogen ($H_2$) sensors. The various embodiments provided herein include a metal-organic framework (MOF) assembled on palladium (Pd) nanowires (NWs) for highly selective and ultra-fast $H_2$ molecule detection. Palladium (Pd) metal is a representative $H_2$ sensing material, but its $H_2$ sensing properties are easily degraded by $O_2$ in air. In the present embodiments, as a protective $H_2$ filter-layer, polyhedron particles of Zn based zeolite imidazole framework (ZIF-8) are directly assembled on lithographically patterned Pd NWs, leading to the creation of ZIF-8/Pd NWs bi-layered sensors. The ZIF-8 filter has many micropores (0.34 nm for gas diffusion) which allows for the predominant penetration of hydrogen molecules with a kinetic diameter of 0.289 nm, while relatively larger gas molecules including oxygen (0.345 nm) and nitrogen (0.364 nm), in air, are effectively screened, resulting in superior hydrogen sensing properties. The present Pd NWs filtered by the ZIF-8 membrane (Pd NWs@ZIF-8) exhibited significantly improved $H_2$ responsiveness (7 sec to 1% of $H_2$) and recovery speed (10 sec to 1% of $H_2$) to low concentration ranges of hydrogen at room temperature in air, compared to pristine Pd NWs (164 sec for response and 229 sec for recovery to 1% of $H_2$). Although the hydrogen response (3.47% to 1% of $H_2$) of Pd NWs@ZIF-8 was slightly decreased when compared with pure Pd NWs (5.88% to 1% of $H_2$), the Pd NWs@ZIF-8 showed 20-fold faster recovery and response speed than pristine Pd NWs. The present dramatic and unexpected results can be attributed, in part, to the molecular sieving and acceleration effect of ZIF-8 covered on Pd NWs. These results also rank highest among currently known room temperature Pd based $H_2$ sensors.

FIG. 1 shows a schematic illustration of an exemplary synthesis process 100 of an exemplary Pd NWs@ZIF-8 120, according to embodiments of the present disclosure.

In embodiments, Pd NWs are prepared by using LPNE process as previously described. In embodiments, glass substrates (amorphous silica ($SiO_2$)) are cleaned by using a chromium acid for 24 hours. A thin layer of nickel (Ni) is then deposited (operation 102) on the glass substrate using a metal evaporator. Next, photo-resistor (PR) layers are spin-coated (operation 104) onto the nickel layer on the glass substrate. After a lithography process using a contact mask and ultraviolet exposure, the exposed Ni is etched (operation 106) in a nitric acid to fabricate a horizontal trench 107. Pd NWs 109 are electrodeposited into the trench (107) of Ni, and the residual PR (113) and Ni (111) are removed (not shown) using acetone and nitric acid, respectively. Finally, Pd NWs patterned glass substrates are immersed in (operation 110) a methanol (MeOH) solution which includes Zn precursors ($Zn(NO_3)_2 \cdot 6H_2O$) and 2-methylimidazole (mIM). ZIF-8 (119) is assembled (operation 112) on both Pd NW (115) and a glass substrate (117) by heterogeneous nucleation.

To investigate the deposition of ZIF-8, in embodiments, the assembly time is controlled to 2 hours (2 h), 4 hours (4 h), and 6 hours (6 h). As used herein, Pd NWs@ZIF-8_2 h, 4 h, and 6 h denote Pd NWs@ZIF-8 self-assembled by 2 hours, 4 hours, and 6 hours, respectively. The samples are washed (not shown) using ethanol 5 times to remove residual ZIF-8 which is not tightly bound on the surface, and are then dried (not shown) for 24 hours at RT (room temperature) to activate ZIF-8.

FIGS. 2A-2C illustrate SEM and EDS elemental mapping images of Pd NWs on glass substrate. In embodiments, the morphologies of the samples are analyzed by using scanning electron microscopy (SEM). In FIG. 2A, Pd NWs with a 10 μm of gap are analyzed. The magnified image clearly reveals the rough surface of the Pd NW with an average diameter of 150±50 nm (FIG. 2B). In addition, the SEM image reveals the growth direction of the Pd NW (arrow in FIG. 2B). The Pd element is confirmed by the energy dispersive X-ray spectrometry (EDS) elemental mapping images using SEM (FIG. 2C).

FIGS. 2D-2F illustrate SEM and EDS elemental mapping images of exemplary Pd NWs@ZIF-8_2 h, according to embodiments of the present disclosure. After assembly in MeOH for 2 h, ZIF-8 is directly grown on the Pd NWs (shown in FIGS. 2D and 2E). The surface of the Pd NW is covered by the ZIF-8, and then some ZIF-8 is also deposited on the glass substrate. In addition, there are necking points on the Pd NWs@ZIF-8_2 h (arrows in FIG. 2E), which are caused by the rugged surface of the Pd NW. In the EDS mapping images of Pd NWs@ZIF-8_2 h (FIG. 2F), the elements of Pd, Zn, carbon (C), and nitrogen (N) are observed. Since the glass substrate is hydrophilic, Zn ions can be easily combined with the surface of the glass. Therefore, Zn element was observed on the entire substrates. On the other hand, the mapping images of C and N are predominantly concentrated on a top surface of the Pd NW. Because the organic ligands of ZIF-8, i.e., mIM, is consisted of C, N, and H elements, this result indicates that the growth of ZIF-8 is faster on Pd NWs compared to the glass substrate.

FIGS. 2G-2I illustrate SEM and EDS elemental mapping images of exemplary Pd NWs@ZIF-8_4 h, according to embodiments of the present disclosure. In the case of ZIF-8 assembled for 4 h, ZIF-8 is uniformly grown on both the glass substrate (shown in FIG. 2G) and Pd NWs (shown in FIG. 2H). The background intensity of C and N elements is increased (shown in FIG. 2I) compared to that of Pd NWs@ZIF-8_2 h seen in FIG. 2F.

FIGS. 2J-2L illustrate SEM and EDS elemental mapping images of exemplary Pd NWs@ZIF-8_6 h, according to embodiments of the present disclosure. For Pd NWs@ZIF-8_6 h, thick ZIF-8 film is formed (shown in FIG. 2J), and the slight agglomeration of ZIF-8 is also observed (shown in FIG. 2K). The Pd NW is entirely embedded in the ZIF-8 membrane as shown in the EDS mapping images of FIG. 2L.

Figure 3A:
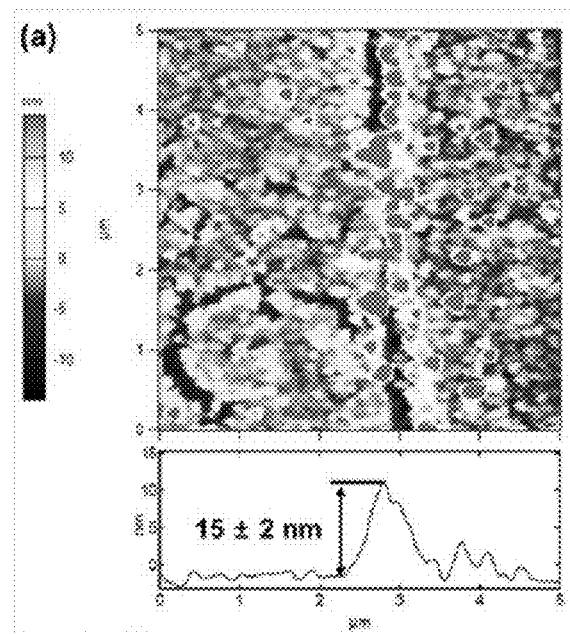
FIG. 3A illustrates an AFM image and depth profile of exemplary Pd NWs.

FIG. 3A illustrates an AFM image and depth profile of exemplary Pd NWs. To clearly investigate the surface morphology of ZIF-8 covered Pd NWs, an atomic force microscope (AFM) analysis was conducted. The height of pristine Pd NWs synthesized by LPNE process is about 15±2 nm (shown in FIG. 3A).

Figure 3B:
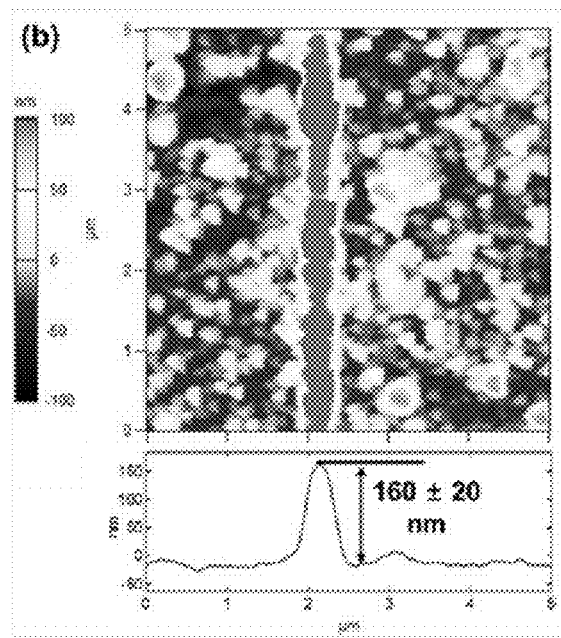
FIG. 3B illustrates an AFM image and depth profile of exemplary Pd NWs@ZIF-8_2 h according to embodiments of the present disclosure.

FIG. 3B illustrates an AFM image and depth profile of exemplary Pd NWs@ZIF-8_2 h according to embodiments of the present disclosure. As shown in FIG. 3B, the height of Pd NWs@ZIF-8_2 h is increased to 160±20 nm, indicating the preferential growth of ZIF-8 on Pd NWs. As the ZIF-8 growth time is increased to 4 h and 6 h, thicker ZIF-8 is uniformly deposited on the surface of the Pd NWs patterned glass substrate.

Figure 3C:
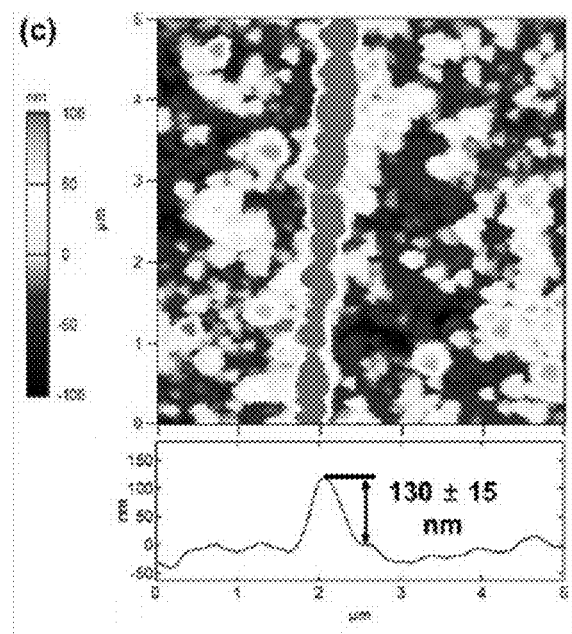
FIG. 3C illustrates an AFM image and depth profile of exemplary Pd NWs@ZIF-8_4 h according to embodiments of the present disclosure.
Figure 3D:
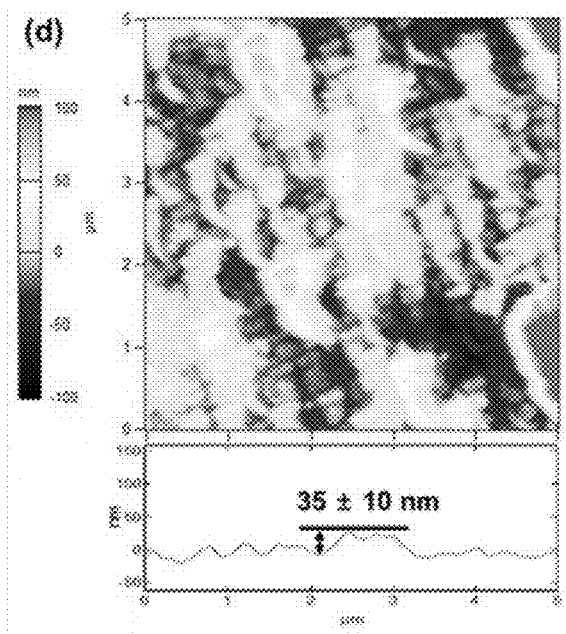
FIG. 3D illustrates an AFM image and depth profile of exemplary Pd NWs@ZIF-8_6 h according to embodiments of the present disclosure.

FIG. 3C illustrates an AFM image and depth profile of exemplary Pd NWs@ZIF-8_4 h according to embodiments of the present disclosure. FIG. 3D illustrates an AFM image and depth profile of exemplary Pd NWs@ZIF-8_6 h according to embodiments of the present disclosure. AFM images reveal that the surface is covered by the ZIF-8 membrane (shown in FIGS. 3C and 3D). As the assembly time increases, the Pd NWs are surrounded by a thicker ZIF-8 layer. However, the height of ZIF-8 on the Pd NW is decreased to 130±15 nm for Pd NWs@ZIF-8_4 h and 35±10 nm for Pd NWs@ZIF-8_6 h, respectively. Since the ZIF-8 is also assembled on the glass substrate, the ZIF-8 thickness on Pd nanowires is not clear in the AFM images.

Figure 3E:
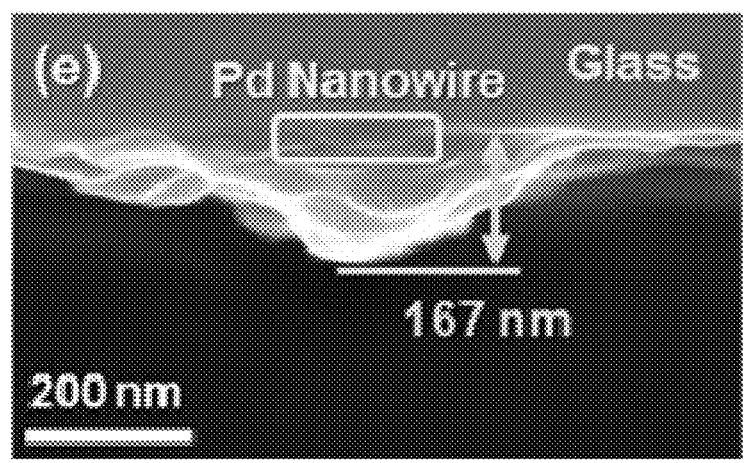
FIG. 3E illustrates a cross-sectional SEM image of exemplary Pd NWs@ZIF-8_2 h according to embodiments of the present disclosure.
Figure 3F:
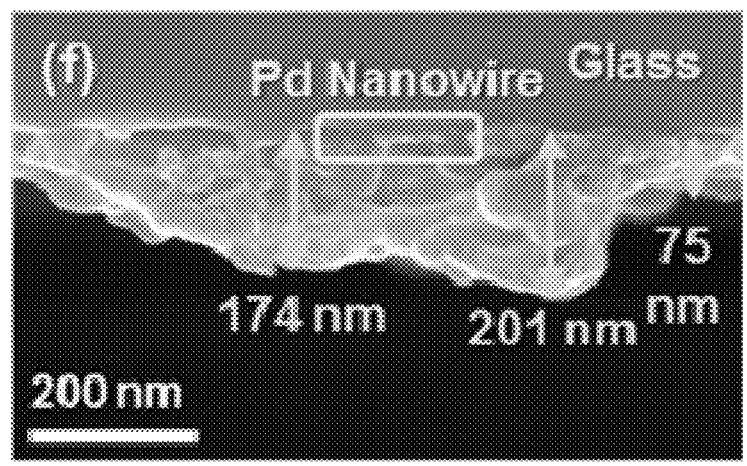
FIG. 3F illustrates a cross-sectional SEM image of exemplary Pd NWs@ZIF-8_4 h according to embodiments of the present disclosure.
Figure 3G:
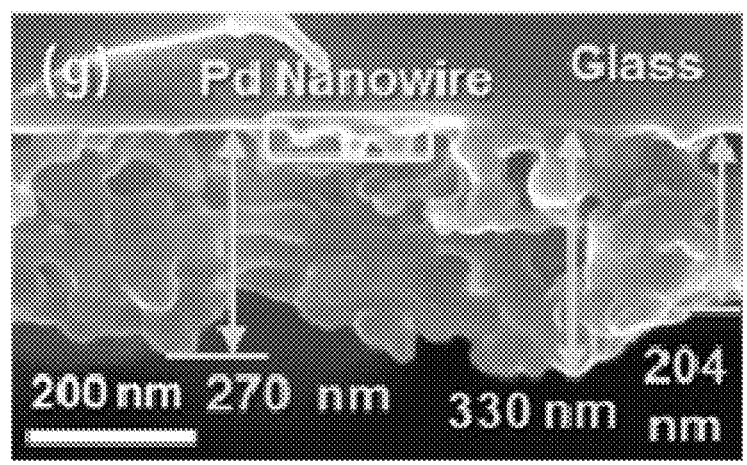
FIG. 3G illustrates a cross-sectional SEM image of exemplary Pd NWs@ZIF-8_6 h according to embodiments of the present disclosure.

FIG. 3E illustrates a cross-sectional SEM image of exemplary Pd NWs@ZIF-8_2 h according to embodiments of the present disclosure. FIG. 3F illustrates a cross-sectional SEM image of exemplary Pd NWs@ZIF-8_4 h according to embodiments of the present disclosure. FIG. 3G illustrates a cross-sectional SEM image of exemplary Pd NWs@ZIF-8_6 h according to embodiments of the present disclosure.

To confirm the thickness of ZIF-8 on the Pd NW patterned glass substrate, cross-sectional SEM analyses of samples is performed. The box in each cross-section image indicates the region which is presumably the Pd NW. FIG. 3E shows that ZIF-8 with a thickness of 167 nm was selectively grown on the surface of the Pd NW after the assembly for 2 h. FIG. 3F shows that, after 4 h of assembly, the thickness of ZIF-8 is slightly increased (201 nm), and ZIF-8 layer also deposited on the glass substrate. FIG. 3G shows that Pd NWs@ZIF-8_6 h showed that all of the Pd NW and glass substrate are covered by the thick layer (330 nm) of ZIF-8.

The growth behavior of ZIF-8 on the Pd NWs and the glass substrate can be described by heterogeneous nucleation. In general, heterogeneous nucleation occurs more easily than homogeneous nucleation, because the critical Gibbs free energy for heterogeneous nucleation is lower than that of homogeneous nucleation. In addition, the sites with high surface energy, such as dislocation, grain boundary, and edge of surface provide higher nucleation rates compared to the sites with smooth surface without any defects. This is because the nucleation of defect sites can reduce the entire energy of the system. Therefore, the Gibbs free energy for nucleation is as follows (equation 3):

$$\Delta G_{Hetero\ on\ defects\ sites} < \Delta G_{Hetero} << \Delta G_{Homo} \qquad (3)$$

In the present embodiments, Pd NWs and the glass substrate act as heterogeneous sites for ZIF-8 nucleation. The Pd NWs synthesized by LPNE process have polycrystalline structure with rough surface while and the glass (SiO$_2$) substrate exhibits a smooth surface due to its amorphous nature and chromium etching process. This means that the Pd NWs have higher internal surface energy than the glass substrate. Therefore, the Gibbs free energy for ZIF-8 nucleation can be described by following equation (equation 4):

$$\Delta G_{ZIF\text{-}8\ on\ Pd} < \Delta G_{ZIF\text{-}8\ on\ glass} << \Delta G_{ZIF\text{-}8\ in\ methanol} \qquad (4)$$

Therefore, ZIF-8 layer is preferentially covered on the surface of Pd NWs compared to the glass substrate (shown in FIGS. 2E and 3E). Pd NWs are electrodeposited by using a horizontal undercut beneath it, thus one side of Pd NW is flat and other side is rough (shown in FIG. 2B). Thus, the growth of ZIF-8 on the rough side is faster than that on the flat side due to the high internal surface energy, leading to the asymmetrical growth of ZIF-8 on Pd NWs (shown in FIGS. 3E-3G). Then, as the assembly time of ZIF-8 increases, because the Pd NWs are already surrounded by ZIF-8, the surface substrate as a heterogeneous nucleation site is also covered by ZIF-8 (shown in FIGS. 2H and 3F), resulting in a decrease of the gap between the ZIF-8 on the Pd NWs and that on the glass substrate (shown in FIGS. 2K and 3G).

Figure 4:
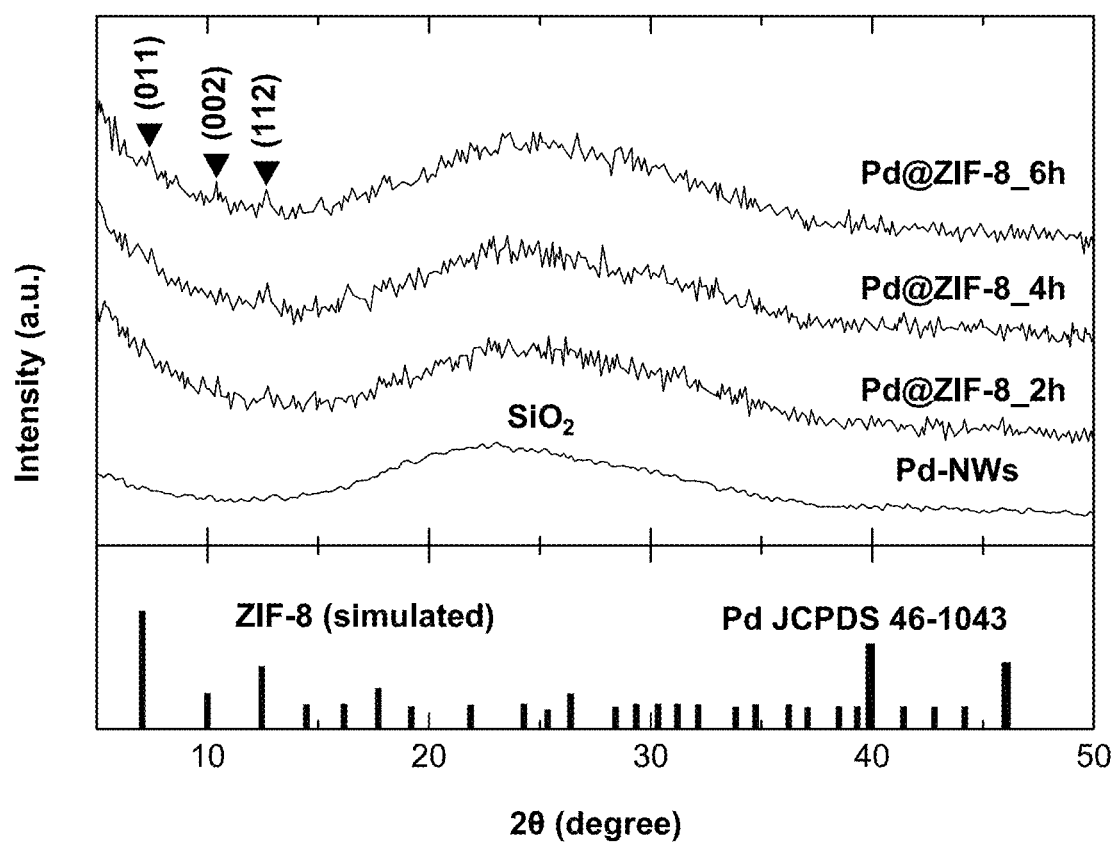
FIG. 4 illustrates GIXRD patterns of exemplary Pd NWs, Pd NWs@ZIF-8_2 h, Pd NWs@ZIF-8_4 h, and Pd NWs@ZIF-8_6 h on glass substrate according to embodiments of the present disclosure.

FIG. 4 illustrates GIXRD patterns of exemplary Pd NWs, Pd NWs@ZIF-8_2 h, Pd NWs@ZIF-8_4 h, and Pd NWs@ZIF-8_6 h on glass substrate according to embodiments of the present disclosure.

The crystal structure of Pd NWs@ZIF-8 is investigated by grazing incidence X-ray diffraction (XRD). As shown in FIG. 4, the peaks related to Pd NWs are not observed in XRD analysis due to the low intensity of Pd (15 (height)× 150 nm (width) with a 10 µm of pattering gap). The background peak is associated with the glass substrate (amorphous SiO$_2$). On the other hand, in case of Pd NWs@ZIF-8 samples, the weak intensities of ZIF-8 main planes of (011), (002), and (112) were observed in the XRD data (marks on FIG. 4), which is consistent with previous studies on ZIF-8.

To further confirm the XRD peaks of ZIF-8, Pd NWs@ZIF-8 samples are prepared and gently washed one time (FIGS. 9A-9D). Since the samples are not fully washed, there are residual Zn sources, mIM, and ZIF-8 which are not bound to the substrates. Thus, the residual Zn sources and mIM can assemble each other and produce the additional ZIF-8 layers on the glass substrate (shown in FIGS. 9A and 9B). The EDS elemental mapping images show the existence of Pd NWs and ZIF-8 on the substrate (shown in FIG. 9C). Although the surface of the sample is slightly agglomerated, the XRD result of the sample clearly shows the ZIF-8 peaks (shown in FIG. 9D), demonstrating the synthesis of ZIF-8 on the substrate.

In order to investigate the critical role of ZIF-8 as molecular sieving layer on Pd NWs, hydrogen gas sensing analysis is carried out by using pristine Pd NWs, Pd NWs@ZIF-8_2 h, Pd NWs@ZIF-8_4 h, and Pd NWs@ZIF-8 6 h. To verify the resistance change, gold (Au) electrodes (gap is 20 µm) are deposited between Pd NWs (shown in FIGS. 10A-10D). The sensing measurement is carried out in the hydrogen concentration range of 0.01 to 1% at RT in air. The dynamic resistance transients of Pd NWs, Pd NWs@ZIF-8_2 h, Pd NWs@ZIF-8_4 h, and Pd NWs@ZIF-8_6 h are shown in FIGS. 5A-5H. The baseline resistance (500Ω for Pd NWs, 20 kΩ for Pd NWs@ZIF-8_2 h, 155 kΩ for Pd NWs@ZIF-8_4 h, and 203 kΩ for Pd NWs@ZIF-8_6 h) of samples is increased as the increasing of the thickness of ZIF-8 layers, which is perhaps caused by the electron trapping of insulating ZIF-8. Since there are defect sites, such as unsaturated coordination sites and vacancies, at the interface between Pd and ZIF-8, the electrons in Pd NWs can easily be trapped in these defects.

Figure 5A:
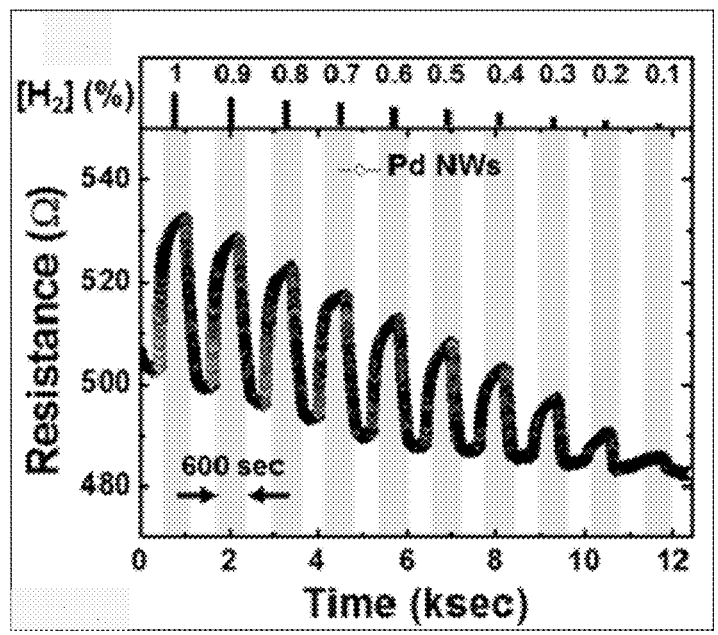
FIGS. 5A and 5B illustrate dynamic baseline resistance transitions in the concentration range of 0.1-1% $H_2$ at RT for exemplary Pd NWs.
Figure 5B:
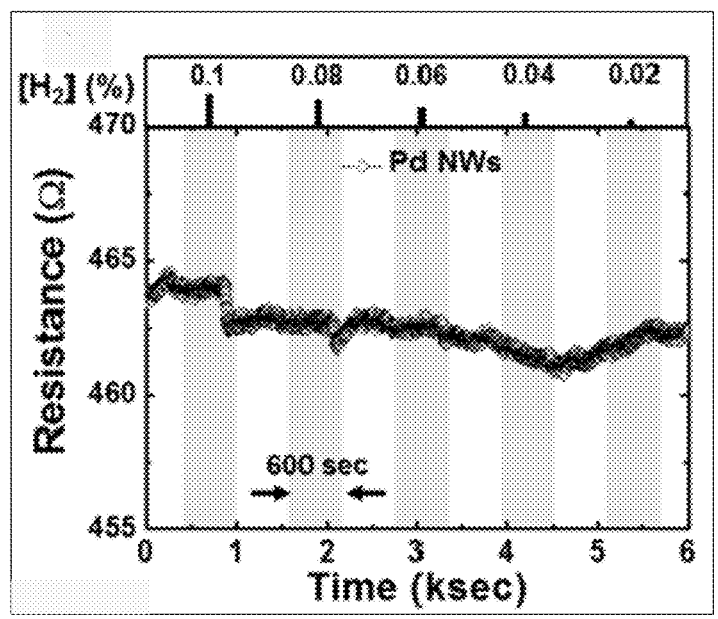
Figure 5C:
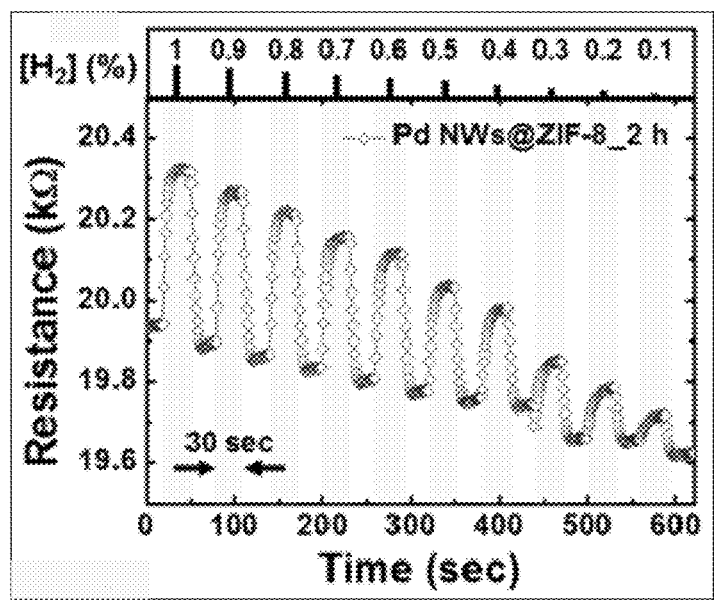
FIGS. 5C and 5D illustrate dynamic baseline resistance transitions in the concentration range of 0.1-1% $H_2$ at RT for exemplary Pd NWs@ZIF-8_2 h according to embodiments of the present disclosure.
Figure 5D:
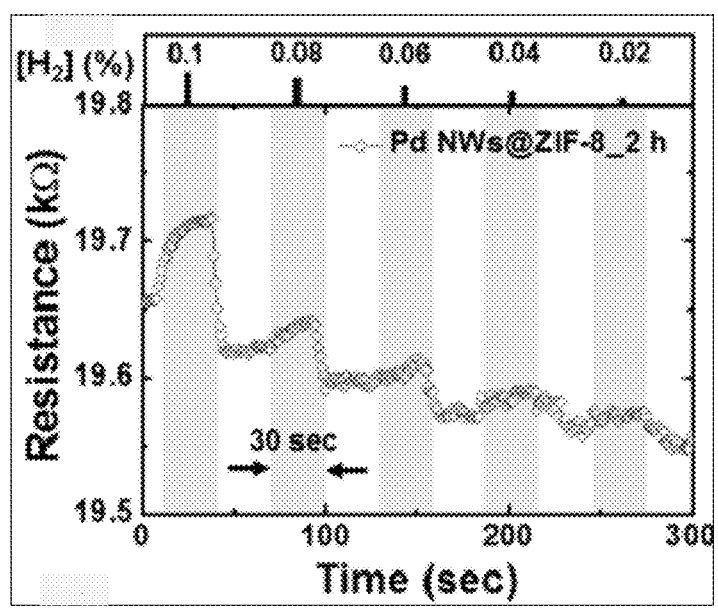
Figure 5E:
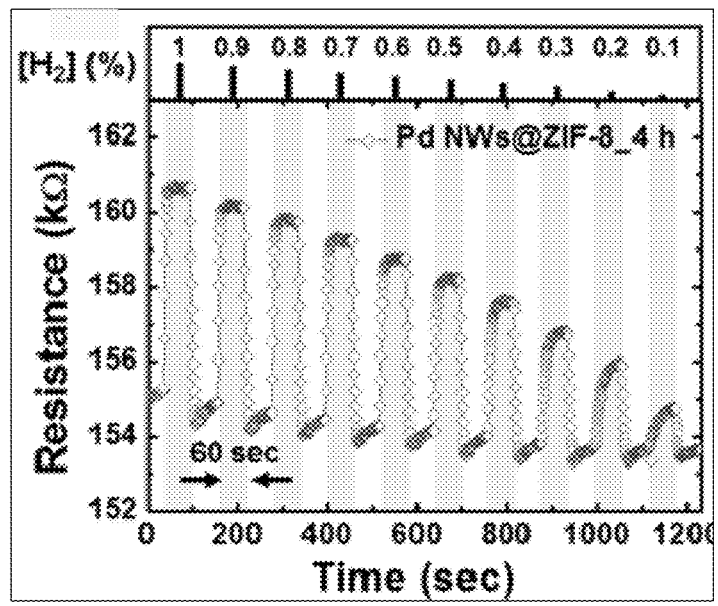
FIGS. 5E and 5F illustrate dynamic baseline resistance transitions in the concentration range of 0.1-1% $H_2$ at RT for exemplary Pd NWs@ZIF-8_4 h according to embodiments of the present disclosure.
Figure 5F:
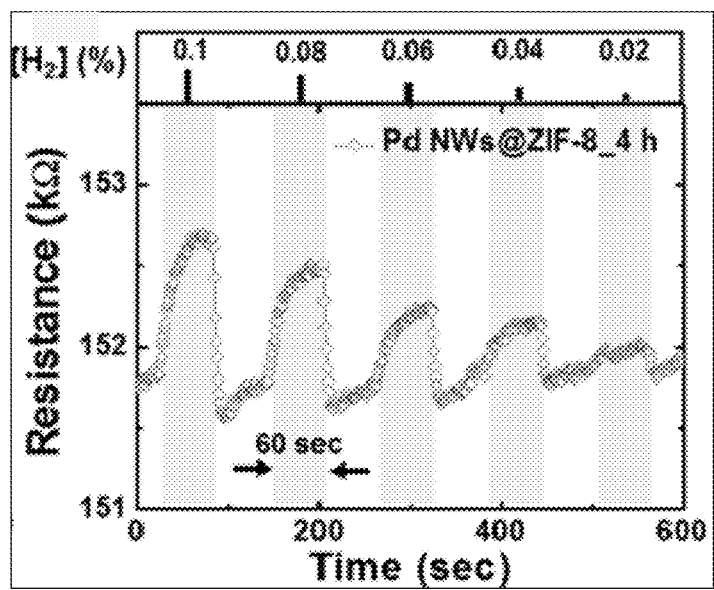
Figure 5G:
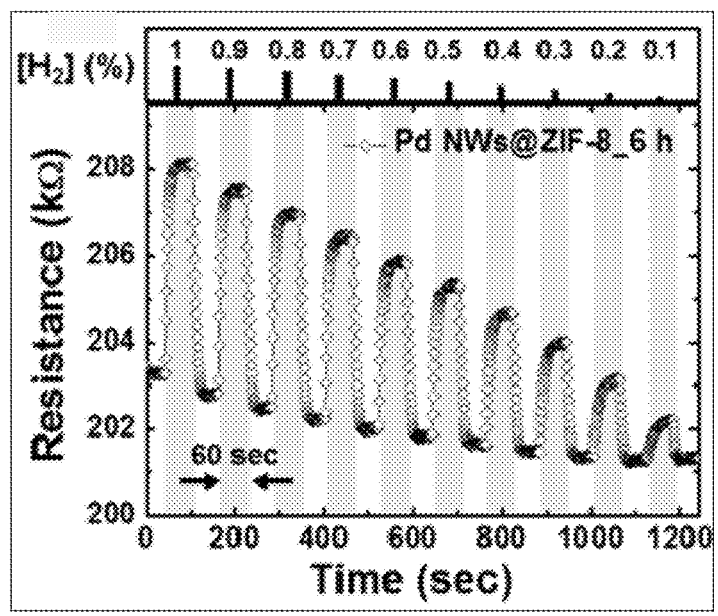
FIGS. 5G and 5H illustrate dynamic baseline resistance transitions in the concentration range of 0.1-1% $H_2$ at RT for exemplary Pd NWs@ZIF-8_6 h according to embodiments of the present disclosure.
Figure 5H:
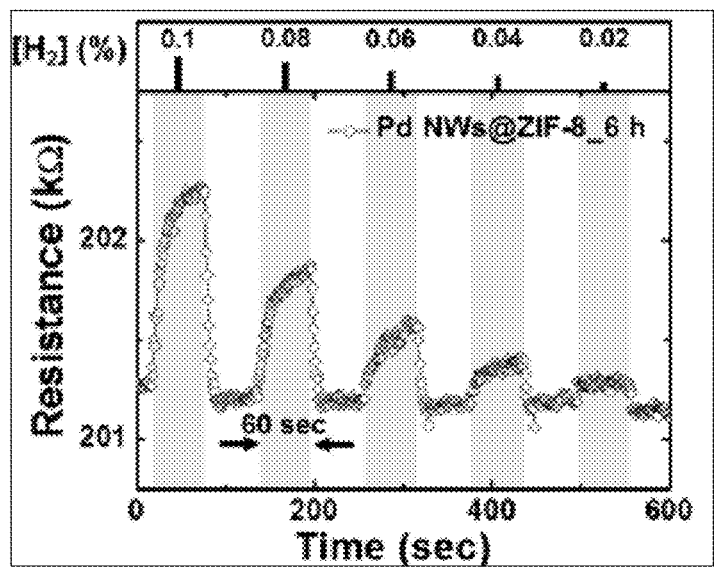

FIGS. 5A and 5B illustrate dynamic baseline resistance transitions in the concentration range of 0.1-1% H$_2$ at RT for exemplary Pd NWs. FIGS. 5C and 5D illustrate dynamic baseline resistance transitions in the concentration range of 0.1-1% H$_2$ at RT for exemplary Pd NWs@ZIF-8_2 h according to embodiments of the present disclosure. FIGS. 5E and 5F illustrate dynamic baseline resistance transitions in the concentration range of 0.1-1% H$_2$ at RT for exemplary Pd NWs@ZIF-8_4 h according to embodiments of the present disclosure. FIGS. 5G and 5H illustrate dynamic baseline resistance transitions in the concentration range of 0.1-1% H$_2$ at RT for exemplary Pd NWs@ZIF-8_6 h according to embodiments of the present disclosure.

The exposure time to hydrogen (for response) and air (for recovery) are observed as 600 sec for Pd NWs, 30 sec for Pd NWs@ZIF-8_2 h, and 60 sec for Pd NWs@ZIF-8_4 h and Pd NWs@ZIF-8_6 h. The pristine Pd NWs exhibit high response for detection of hydrogen at RT in air (shown in FIG. 5A). However, response and recovery of the Pd NWs are extremely slow. The resistance change of Pd NWs is rapidly decreased when exposed to low levels (0.1-0.2%) of hydrogen. In addition, the Pd NWs do not exhibit the sensing properties below 0.1% of hydrogen (shown in FIG. 5B). The periodic decrease of the baseline resistance after hydrogen exposure is not yet known, but this phenomenon was also observed in the previous literatures.

On the other hand, the Pd NWs@ZIF-8 samples exhibited very fast resistance variations (shown in FIGS. 5C-5H). They show stable resistance transients even in short-terms of exposure time (30 sec for Pd NWs@ZIF-8_2 h, and 60 sec for Pd NWs@ZIF-8_4 h and Pd NWs@ZIF-8_6 h). Considering that the stable dynamic resistance transients of Pd NWs are obtained at an exposure time of 600 sec, remarkably reduced response and recovery times of Pd NWs are achieved via molecular sieving of the ZIF-8 membrane. The Pd NWs@ZIF-8_2 h showed fastest response and recovery speed (shown in FIG. 5C) among the Pd NWs@ZIF-8, but the sensor did not detect the low level of hydrogen molecules (shown in FIG. 5D). However, the detection limit of Pd NWs@ZIF-8_4 h and Pd NWs@ZIF-8_6 h is observed as down to 0.06% (600 part per million) while maintaining reasonably high response and recovery speed (shown in FIGS. 5E-5H). The hydrogen sensing properties at concentrations of less than 0.04% of hydrogen were not accurately identified due to the resistance change from the noise. Therefore, in embodiments, the limit of detection of the sensors may be defined as 0.06% for both Pd NWs@ZIF-8_4 h and Pd NWs@ZIF-8_6 h.

Figure 6A:
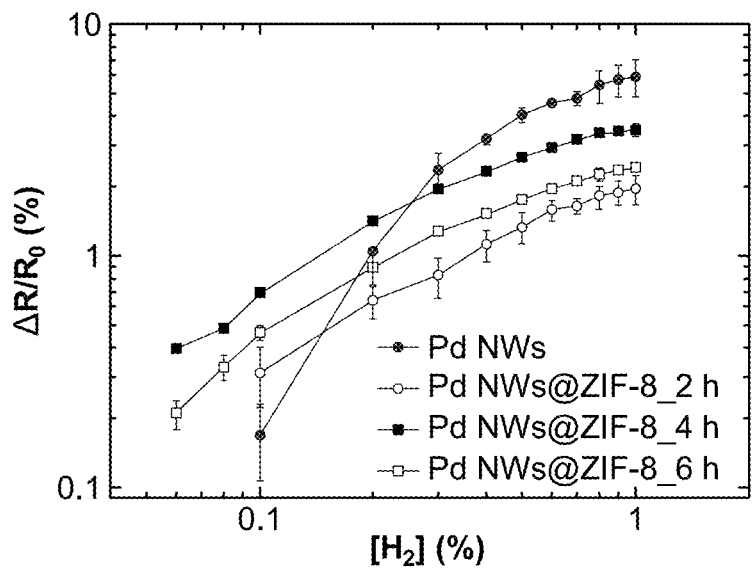
FIG. 6A illustrates hydrogen sensing metrics (sensitivity versus $H_2$ in air) for exemplary Pd NWs, Pd NWs@ZIF-8_2 h, Pd NWs@ZIF-8_4 h, and Pd NWs@ZIF-8_6 h according to embodiments of the present disclosure.
Figure 6B:
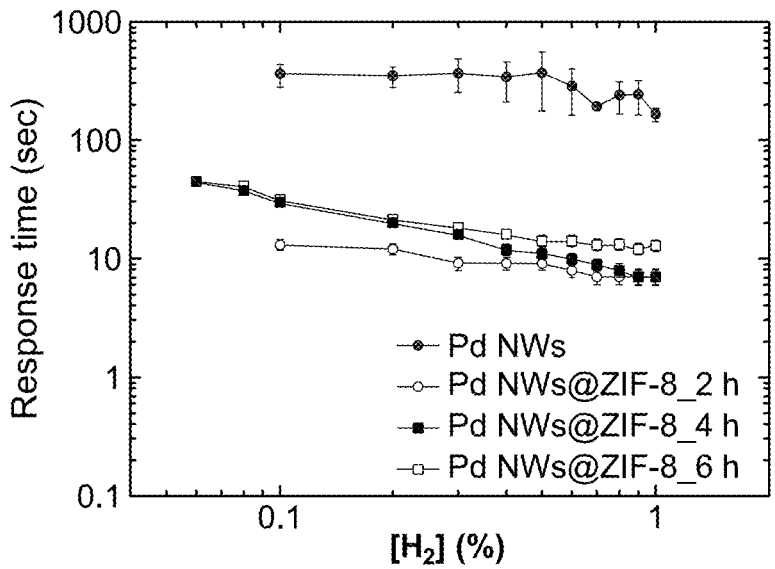
FIG. 6B illustrates hydrogen sensing metrics (response time versus $H_2$ in air) for exemplary Pd NWs, Pd NWs@ZIF-8_2 h, Pd NWs@ZIF-8_4 h, and Pd NWs@ZIF-8_6 h according to embodiments of the present disclosure.
Figure 6C:
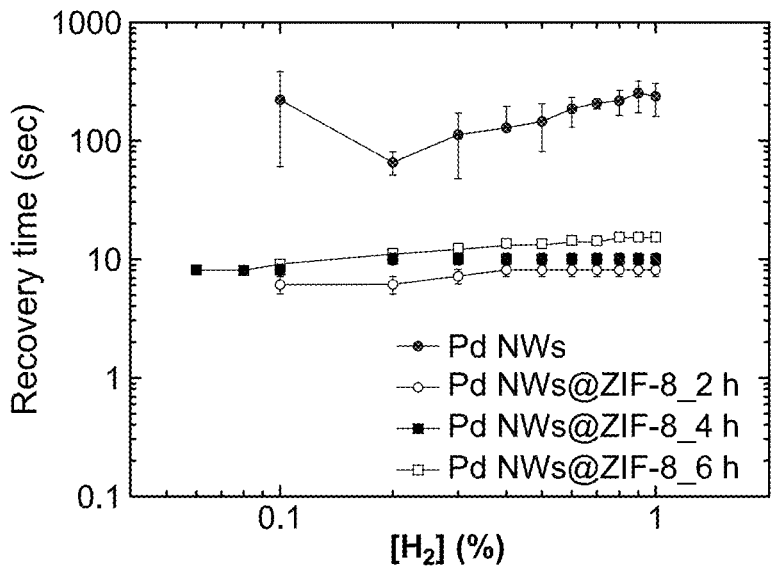
FIG. 6C illustrates hydrogen sensing metrics (recovery time versus $H_2$ in air) for exemplary Pd NWs, Pd NWs@ZIF-8_2 h, Pd NWs@ZIF-8_4 h, and Pd NWs@ZIF-8_6 h according to embodiments of the present disclosure.

FIG. 6A illustrates hydrogen sensing metrics (sensitivity versus H$_2$ in air) for exemplary Pd NWs, Pd NWs@ZIF-8_2 h, Pd NWs@ZIF-8_4 h, and Pd NWs@ZIF-8_6 h according to embodiments of the present disclosure. FIG. 6B illustrates hydrogen sensing metrics (response time versus $H_2$ in air) for exemplary Pd NWs, Pd NWs@ZIF-8_2 h, Pd NWs@ZIF-8_4 h, and Pd NWs@ZIF-8_6 h according to embodiments of the present disclosure. FIG. 6C illustrates hydrogen sensing metrics (recovery time versus $H_2$ in air) for exemplary Pd NWs, Pd NWs@ZIF-8_2 h, Pd NWs@ZIF-8_4 h, and Pd NWs@ZIF-8_6 h according to embodiments of the present disclosure. To clearly compare sensing properties, gas response, response time, and recovery time of the 4 different sensors, i.e., pure Pd NWs, Pd NWs@ZIF-8_2 h, Pd NWs@ZIF-8_4 h, and Pd NWs@ZIF-8_6 h, respectively, are characterized. The response of sensors is defined as the ratio ($\Delta R_{max}/R_0(\%)$) of maximum resistance change ($\Delta R_{max}$) to baseline resistance ($R_0$). Response and recovery times are the time necessary for the resistance to increase from $R_0$ to the 0.9 $\Delta R_{max}$ and the time for the resistance to decrease from $\Delta R_{max}$ to 0.1 $R_0$, respectively. The hydrogen responses of the sensors are plotted in FIG. 6A. In the range of 0.3-1% hydrogen, the Pd NWs exhibited higher response than the Pd NWs@ZIF-8. To 1% of hydrogen, the response of each sample is 5.88% for pristine Pd NWs, 1.93% for Pd NWs@ZIF-8_2 h, 3.47% for Pd NWs@ZIF-8_4 h, and 2.39% for Pd NWs@ZIF-8_6 h, respectively. However, the response of Pd NWs is rapidly decreased in low levels (0.1-0.2%) of hydrogen. The rapid decrease in response of Pd NW is explained by the oxygen effect in air. Oxygen can react with adsorbed hydrogen on the surface of Pd (see equations 1 and 2), and at low concentrations, the response may be greatly affected by the reaction. Thus, the response is drastically decreased. On the other hand, Pd NWs@ZIF-8 samples exhibited higher sensitivity (0.31% for Pd NWs@ZIF-8_2 h, 0.69% for Pd NWs@ZIF-8_4 h, and 0.46% for Pd NWs@ZIF-8 6 h) than Pd NWs (0.17%) to 0.1% of hydrogen. In addition, Pd NWs@ZIF-8 4 h shows higher response than Pd NWs@ZIF-8_2 h and Pd NWs@ZIF-8_6 h in the all range of hydrogen.

Figure 7A:
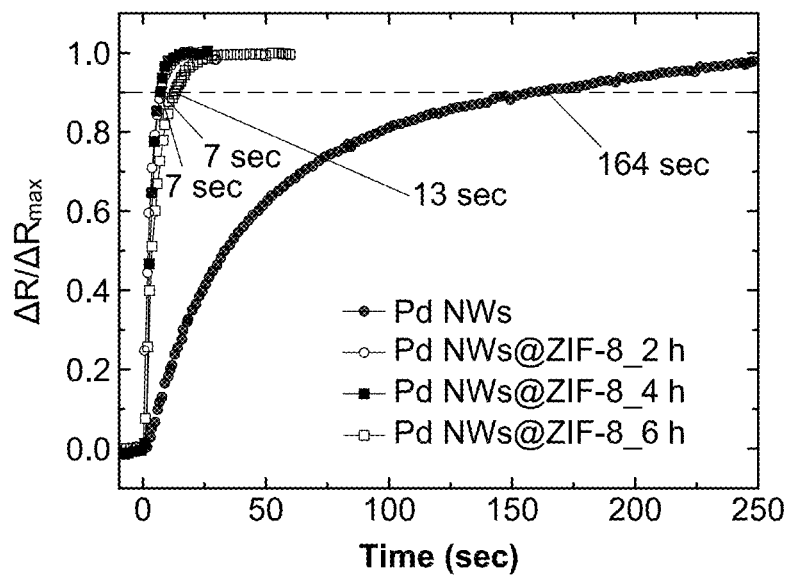
FIG. 7A illustrates a normalized curve of response time for exemplary Pd NWs, Pd NWs@ZIF-8_2 h, Pd NWs@ZIF-8_4 h, and Pd NWs@ZIF-8_6 h (with 1% $H_2$ in air) according to embodiments of the present disclosure.
Figure 7B:
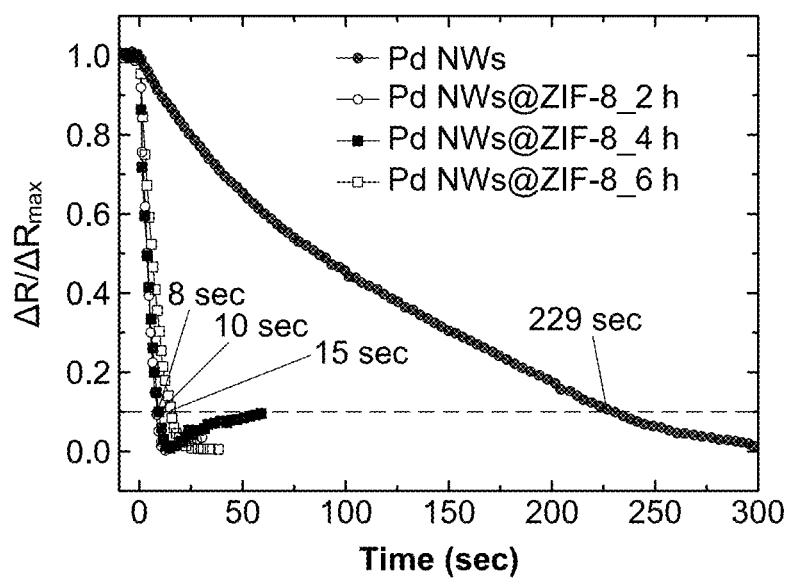
FIG. 7B illustrates a normalized curve of recovery time for exemplary Pd NWs, Pd NWs@ZIF-8_2 h, Pd NWs@ZIF-8_4 h, and Pd NWs@ZIF-8_6 h (with 1% $H_2$ in air) according to embodiments of the present disclosure.

FIG. 7A illustrates a normalized curve of response time for exemplary Pd NWs, Pd NWs@ZIF-8_2 h, Pd NWs@ZIF-8_4 h, and Pd NWs@ZIF-8_6 h (with 1% $H_2$ in air) according to embodiments of the present disclosure. FIG. 7B illustrates a normalized curve of recovery time for exemplary Pd NWs, Pd NWs@ZIF-8_2 h, Pd NWs@ZIF-8_4 h, and Pd NWs@ZIF-8_6 h (with 1% $H_2$ in air) according to embodiments of the present disclosure.

In FIGS. 7A and 7B, the horizontal dashed line indicates $\Delta R/R_{max}=0.90$ for response and $\Delta R/R_{max}=0.1$ for recovery. The response and recovery time of sensors are dramatically improved by the ZIF-8 layer (FIGS. 6B and 6C). Pd NWs exhibit a sluggish reaction rate, which is consistent with previous evaluations of Pd NW based hydrogen sensors. On the other hand, Pd NWs@ZIF-8 accelerated the response and recovery times of hydrogen detection. The response time to 1% of hydrogen is 7 sec for Pd NWs@ZIF-8_2 h and Pd NWs@ZIF-8_4 h, and 13 sec for Pd NWs@ZIF-8_6 h, while that of Pd NWs is 164 sec (shown in FIG. 7A). In addition, the recovery time toward 1% of hydrogen is 8 sec for Pd NWs@ZIF-8_2 h, 10 sec for Pd NWs@ZIF-8_4 h, 15 sec for Pd NWs@ZIF-8_6 h, and 229 sec for Pd NWs (shown in FIG. 7B). Although the response time of Pd NWs@ZIF-8 is slightly increased in the low concentration range, the response of Pd NWs@ZIF-8 is faster than that of Pd NWs by over 10-fold (shown in FIG. 6B). In addition, the recovery time of the sensors in the low concentration range is further decreased. The sensing properties of other Pd based materials operated at RT in air are summarized in Table 1. Although the response of Pd NWs@ZIF-8 is lower than other Pd based sensors in previous studies, response time and recovery time of the sensors is extremely fast. The Pd NWs@ZIF-8 far exceed known systems, in terms of response and recovery time.

Figures 8A, 8B, 8C:
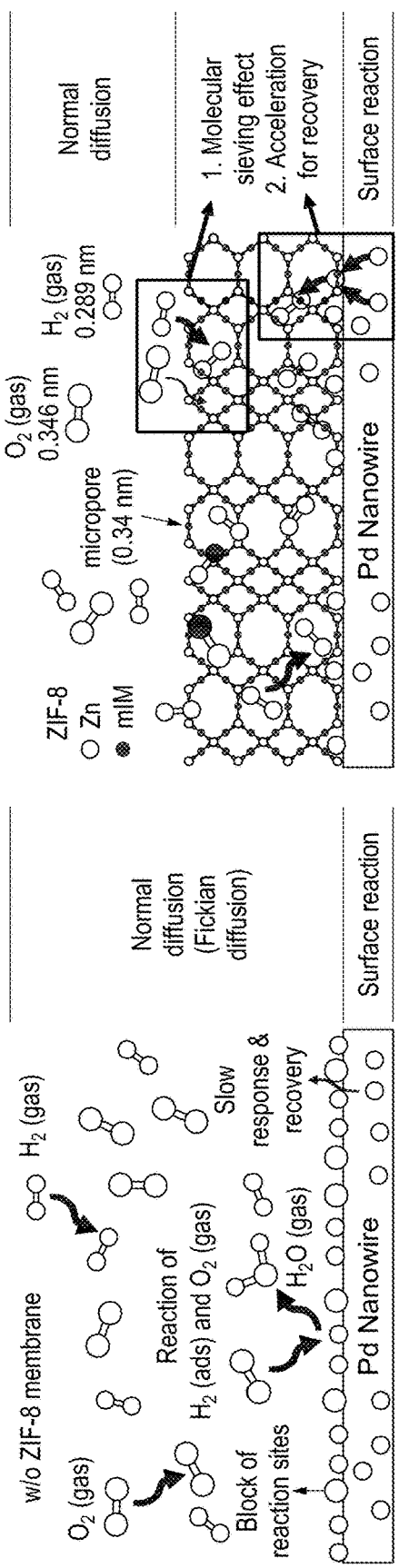
FIG. 8A shows a schematic illustration of a sensing model for Pd NWs without ZIF-8 membrane.
FIG. 8B shows a schematic illustration of a sensing model for exemplary Pd NWs@ZIF-8 according to embodiments of the present disclosure.
FIG. 8C shows a schematic illustration of exemplary Pd NW, Pd NWs@ZIF-8_2 h, Pd NWs@ZIF-8_4 h, and Pd NWs@ZIF-8_6 h according to embodiments of the present disclosure.

FIG. 8A shows a schematic illustration of a sensing model for Pd NWs without ZIF-8 membrane. In case of Pd NWs, hydrogen and oxygen diffuse to the surface of Pd NWs, and they react with Pd NWs. However, oxygen can react with adsorbed hydrogen, and adsorbed oxygen can block the active site of Pd NWs, leading to the rapid decrease in sensing properties, including response, recovery, and detection limit, of Pd NWs.

FIG. 8B shows a schematic illustration of a sensing model for exemplary Pd NWs@ZIF-8 according to embodiments of the present disclosure. Pd NWs without ZIF-8 can be largely affected by oxygen in air. However, the micropores (0.34 nm) of ZIF-8 can act as a molecule-sieving layer. Hydrogen (kinetic diameter of 0.298 nm) easily diffuses through the cavity of ZIF-8, while oxygen (kinetic diameter of 0.346 nm) diffusion in ZIF-8 is retarded. The hydrogen that diffuses to the surface of Pd NWs can react with Pd. In addition, ZIF-8 can improve the response rate of the sensors by the acceleration effect.

Since the gas molecules permeate through the micropores (0.34 nm) of ZIF-8, hydrogen with a kinetic diameter of 0.289 nm has high permeability in the ZIF-8 membrane, while the permeability of large sized molecules is low. Therefore, the ZIF-8 membrane on Pd NWs can effectively minimize the reaction of oxygen molecules (a kinetic diameter of 0.345 nm) on Pd. In addition, the introduction of MOF on Pd crystals can increase the adsorption and desorption rate of hydrogen in Pd by enhancing the surface/bulk reactivity of the nanocrystals. Moreover, ZIF-8 can contain hydrogen in its porous structure at low temperature (1.3 wt % $H_2$ at 77 K), because hydrogen molecules are easily physisorbed on the organic ligand (mIM) sites of ZIF-8 with the low heat (~4.5 kJ/mol) for an initial adsorption. At room temperature, although the physisorbed hydrogen with relatively high thermal energy can diffuse easily through the microporous channels of ZIF-8, the physisorption sites of ZIF-8 on the Pd NWs can help the desorption of hydrogen on the surface of the Pd NWs. Since the intermediate state (physisorption sites in ZIF-8) is generated in the overall reaction of hydrogen desorption, the total activation energy of hydrogen desorption can be decreased by the catalytic effect. Due to these effects, Pd NWs@ZIF-8 dramatically improves the hydrogen sensing properties in terms of detection limit, response time, and recovery time.

Figure 8F:
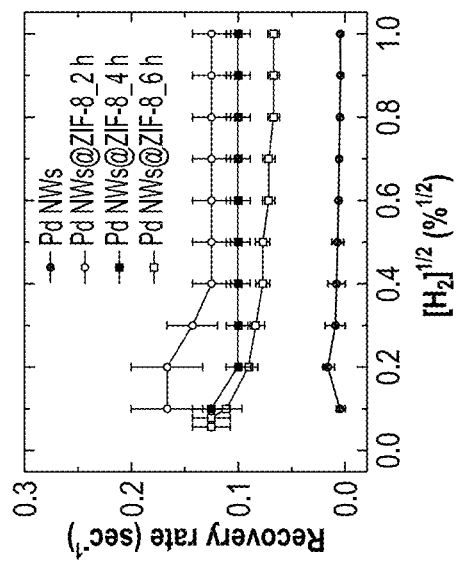
FIG. 8F illustrates recovery rate versus $H_2$ in air according to embodiments of the present disclosure.

FIG. 8C shows a schematic illustration of exemplary Pd NW, Pd NWs@ZIF-8 2 h, Pd NWs@ZIF-8_4 h, and Pd NWs@ZIF-8_6 h according to embodiments of the present disclosure. FIG. 8D illustrates exemplary sensitivity versus $H_2^{1/2}$ in air according to embodiments of the present disclosure.

When the Pd NW without protection layer is exposed to the air, the surface of Pd NW is affected by oxygen molecules. In case of Pd NWs@ZIF-8_2 h, the Pd NW is covered by ZIF-8, but there are necking points in the Pd NWs@ZIF-8, which is observed in SEM images (shown in FIG. 2E). When the necking points are exposed to oxygen, the adsorbed oxygen on the necking points can block the reaction sites of the Pd NW. In addition, since the growth of ZIF-8 on Pd NWs can reduce the active sites of the Pd NWs, the response of Pd NWs@ZIF-8_2 h is decreased compared to the pristine Pd NWs. On the other hand, in case of Pd NWs@ZIF-8_4 h, the Pd NW is fully-covered by the ZIF-8 layers (shown in FIG. 2H), which minimizes the negative effect of oxygen on Pd based hydrogen sensors. As a result, the response of Pd NWs@ZIF-8_4 h is higher than that of Pd NWs@ZIF-8_2 h. However, Pd NWs@ZIF-8_4 h shows still low response compared to the pristine Pd NWs because of the decrease in the reaction sites of Pd NWs caused by the growth of ZIF-8. After the assembly of ZIF-8 for 6 h, the thick layer of ZIF-8 is deposited on the surface, and the Pd NW is embedded in the ZIF-8 layers (shown in FIG. 2K). Since the amounts of hydrogen diffused to the surface of Pd NWs is decreased compared to Pd NWs@ZIF-8_4 h, the response of Pd NWs@ZIF-8_6 h is decreased. In terms of response and recovery, the sensors exhibit clear tendencies: i) ZIF-8 decreases the response and recovery time of Pd NWs, because ZIF-8 plays a role of the molecular sieving and acceleration layer; and ii) The thick ZIF-8 layer increases the response and recovery time, because the diffusion length of hydrogen in ZIF-8 layer is increased.

To further demonstrate the improvement of sensors, the response and response rate of the sensors is plotted linearly versus $H_2^{1/2}$. Response rate is defined as a reciprocal of response time. Since the detection of hydrogen below 1% is explained by hydrogen diffusion into interstitial sites of Pd metals ($\alpha$-PdH$_x$), the relation between hydrogen concentration (below 1%) and response of Pd NWs can be described by Sievert's Law. The reaction of hydrogen on Pd NWs and the equilibrium constant (K) of the reaction can be written as following equations (reaction 5 and equation 6).

$$0.5\ H_2(gas) \rightarrow H(ads) \quad (5)$$

$$K = (\sqrt{P_{H_2}})/(x_S) \quad (6)$$

For small values of $x_s$ ($x<0.015$), it can be assumed that $x_s \approx x$. In addition, the electrical resistivity of $\alpha$-PdH$_x$ is directly proportional to adsorbed hydrogen ($x_s$). Therefore, the resistance change of Pd NWs is linearly proportional to $H_2^{1/2}$ ($\Delta R/R_0 \propto H_2^{1/2}$). Since the response to 0% of $H_2$ should be 0, the sensing data is plotted with the assumption that the intercept of the y-axis is 0 (shown in FIG. 8D). In other words, it should exhibit linear relationship. However, oxygen in air and ZIF-8 layer on Pd NWs can influence on the reaction of Pd, leading to non-ideal behavior. In case of pristine Pd NWs, an ideal relationship is observed up to 0.5% of hydrogen. However, after then, the sensor shows a non-ideal behavior, which can be explained that the Pd NWs can be largely influenced by oxygen in low level of hydrogen. On the other hand, when ZIF-8 layer is covered on Pd NWs, the ideal behavior of the sensors is shown up to 0.4% H$_2$ for Pd NWs@ZIF-8_2 h, and 0.2% H$_2$ for Pd NWs@ZIF-8_4 h and Pd NWs@ZIF-8_6 h. In addition, the detection limit of sensors is down to 0.06% for Pd NWs@ZIF-8_4 h and Pd NWs@ZIF-8_6 h, compared to that (0.1%) of Pd NWs. These results demonstrate that ZIF-8 membrane minimizes the oxygen effect on Pd NWs by the molecular sieving effect.

Figure 8E:
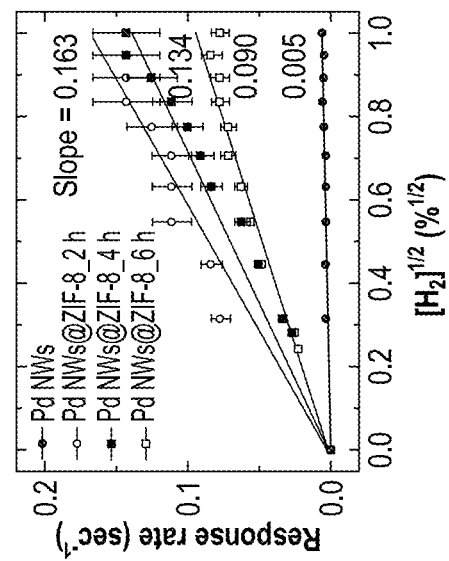
FIG. 8E illustrates exemplary response rate versus $H_2^{1/2}$ in air according to embodiments of the present disclosure.
Figure 8D:
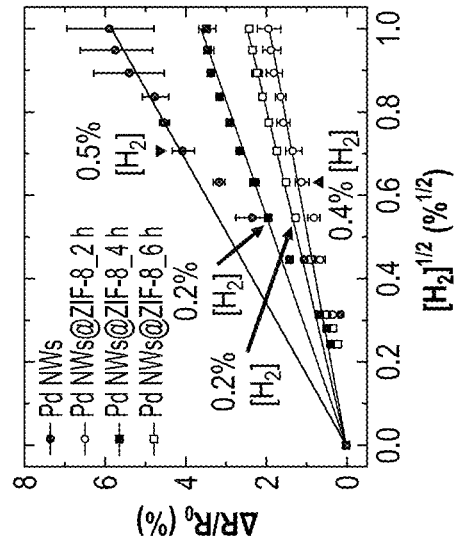
FIG. 8D illustrates exemplary sensitivity versus $H_2^{1/2}$ in air according to embodiments of the present disclosure.

FIG. 8E illustrates exemplary response rate versus $H_2^{1/2}$ in air according to embodiments of the present disclosure. FIG. 8F illustrates recovery rate versus H$_2$ in air according to embodiments of the present disclosure.

Previously, Yang et al. demonstrated the linear relationship between response rate of Pd NWs and $H_2^{1/2}$ in the concentration below 1% of hydrogen. The slope of each plotting line according to the present embodiments resulted in obtained higher values for Pd NWs@ZIF-8 than Pd NWs. In particular, the slope of Pd NWs@ZIF-8_2 h is 32.6-fold higher than pristine Pd NWs. Since the slope directly represents the response speed of the sensors, it is confirmed herein that ZIF-8 layer improves the response speed of Pd NWs while the increase of ZIF-8 thickness retards the response. Furthermore, the recovery rate of sensors is shown in FIG. 8F. Recovery time of sensors is defined as a reciprocal of response time. As similar with the response rate, a noticeable improvement is observed in the response rate of Pd NWs@ZIF-8, comparing to that of Pd NWs. In general, when $\alpha$-PdH$_x$ is exposed to air for recovery, the adsorbed hydrogen is diffused out from the Pd NWs to the air. However, since the physisorption sites of the ZIF-8 near the Pd NWs can accelerate the desorption of hydrogen on the Pd NWs, the response rate of the sensors is improved when the Pd NWs are covered with the ZIF-8 layer. In addition, the recovery rate of Pd NWs@ZIF-8 is increased at low level (below 0.4%) of hydrogen compared to high level (above 0.4%) of hydrogen. Since the physisorption sites of ZIF-8 on Pd NWs can act as a catalyst for the desorption of hydrogen in Pd, the recovery rate of Pd NWs@ZIF-8 is faster at low concentration due to the small amounts of adsorbed hydrogen in Pd. Although it is not readily explained by this mechanism, these results apparently show that the presence of ZIF-8 layer on Pd dramatically enhances the recovery and response rates of the Pd NWs by the molecular sieving effect and the acceleration effect of ZIF-8.

FIG. 9A illustrates AFM and depth profiles of exemplary Pd NWs. FIG. 9B illustrates AFM and depth profiles of exemplary Pd NWs@ZIF-8_2h, according to embodiments of the present disclosure. FIG. 9C illustrates AFM and depth profiles of exemplary Pd NWs@ZIF-8_4h, according to embodiments of the present disclosure FIG. 9D illustrates AFM and depth profiles of exemplary Pd NWs@ZIF-8 6h, according to embodiments of the present disclosure FIG. 9E illustrates a cross-sectional SEM image of exemplary Pd NWs@ZIF-8_2h, according to embodiments of the present disclosure FIG. 9F illustrates a cross-sectional SEM image of exemplary Pd NWs@ZIF-8_4h, according to embodiments of the present disclosure FIG. 9G illustrates a cross-sectional SEM image of exemplary Pd NWs@ZIF-8_6h, according to embodiments of the present disclosure. FIGS. 9A-9G are discussed above.

Figure 10A:
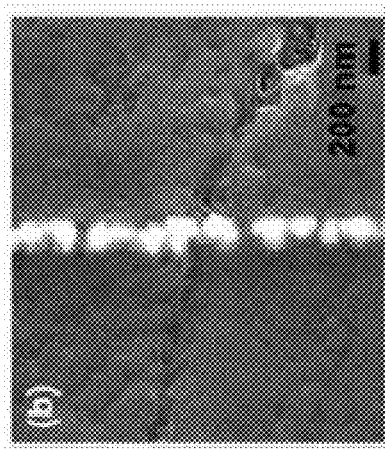
FIG. 10A illustrates an SEM image of exemplary Pd NWs@ZIF-8 according to embodiments of the present disclosure.
Figure 10B:
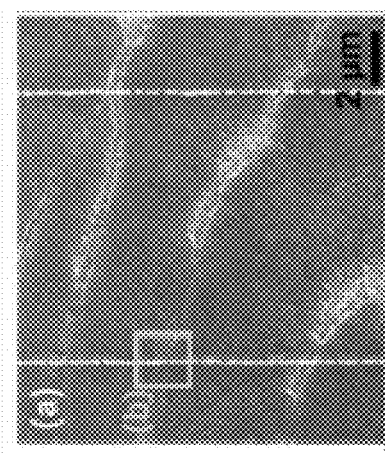
FIG. 10B illustrates an SEM image of exemplary Pd NWs@ZIF-8 according to embodiments of the present disclosure.
Figure 10C:
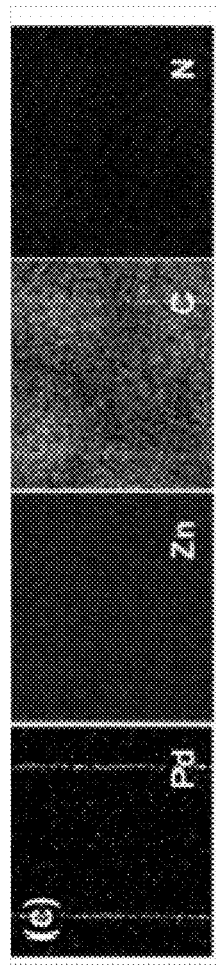
FIG. 10C illustrates EDS images of exemplary Pd NWs@ZIF-8 according to embodiments of the present disclosure.
Figure 10D:
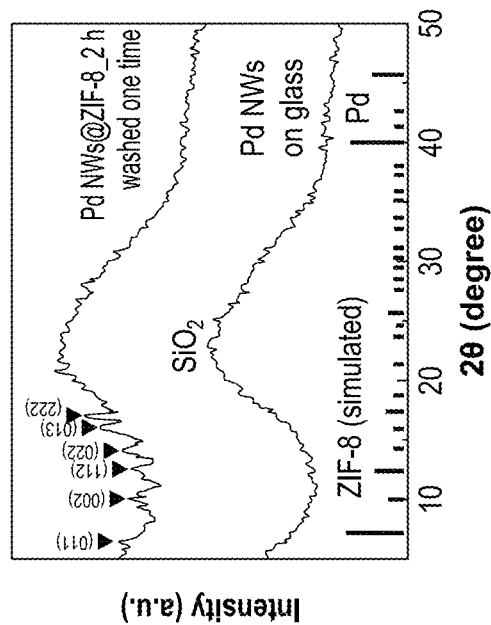
FIG. 10D illustrates XRD data of exemplary Pd NWs@ZIF-8 according to embodiments of the present disclosure.

FIG. 10A illustrates an SEM image of exemplary Pd NWs@ZIF-8 according to embodiments of the present disclosure. FIG. 10B illustrates an SEM image of exemplary Pd NWs@ZIF-8 according to embodiments of the present disclosure. FIG. 10C illustrates EDS images of exemplary Pd NWs@ZIF-8 according to embodiments of the present disclosure. FIG. 10D illustrates XRD data of exemplary Pd NWs@ZIF-8 according to embodiments of the present disclosure. FIGS. 10A-10D are discussed above.

TABLE 1

Sensing properties for Pd based hydrogen sensors operated at room temperature in air.

| Materials[a] | Response @ H$_2$ 0.1% | $\tau_{resp}/\tau_{rec}$[b] @ H$_2$ 0.1% | Detection limit (H$_2$) |
|---|---|---|---|
| Pd/Ni film (t = 50 nm) | nr | 120 sec/20 sec | nr |
| Pd NW (d= 50-80 nm) | ~1% | nr | 1000 ppm |
| Single Pd NW (25 (h) × 85 nm (w)) | 3% | 400 sec/1000 sec | 100 ppm |
| Single Pd@Pt NW (40 (h) × 100 nm (w)) | nr | 250 sec/15 sec | 0.2% |
| Pd nanotube | 2% | 80 sec/nr | 500 ppm |
| Pd nanotube | 1000% | 190 sec/nr | 100 ppm |

TABLE 1-continued

Sensing properties for Pd based hydrogen sensors operated at room temperature in air.

| Materials[a] | Response @ $H_2$ 0.1% | $\tau_{resp}/\tau_{rec}$[b] @ $H_2$ 0.1% | Detection limit ($H_2$) |
|---|---|---|---|
| Pd NWs@ZIF-8_2 h | 0.3% | 13 sec/6 sec | 1000 ppm |
| Pd NWs@ZIF-8_4 h | 0.7% | 30 sec/8 sec | 600 ppm |

[a]Abbreviations: t = thickness, d = diameter, (h) and (w) are the lateral dimensions of a NW with a rectangular cross section, nr = not reported.
[b]$\tau_{resp}$ is the time necessary for the resistance to increase from $R_0$ to the 0.9$\Delta R_{max}$, and $\tau_{rec}$ is the time for the resistance to decrease from $\Delta R_{max}$ to 0.1$R_0$.

EXPERIMENTAL SECTIONn

Materials. 2-methylimidazole (mIM, 99.0%) were purchased from Aldrich. Zinc nitrate hexahydrate ([Zn(NO$_3$)$_2$·6H$_2$O], 98%), palladium chloride (PdCl$_2$, 99.999%), ethylenediaminetetraacetic acid (EDTA, 99.995%), potassium chloride (KCl, 99.3%) were used as received from Sigma-Aldrich. Positive photoresist solution (Shipley S1808) and developer solution (Shipley MF-319) were purchased from Microchem. Glass substrates, acetone, methanol, and nitric acid were used as received from Fisher. Nickel (Ni) and gold (Au) targets (99.999%) were purchased from Kurt J. Lesker.

Synthesis of Pd NWs. Pd NWs with width of 150 nm and height of 15 nm were fabricated by LPNE process. The interval distance between each Pd NWs was 10 μm. Firstly, Ni films with a thickness of 40 nm was deposited on glass substrates by using thermal evaporator. A positive photoresist (Shipley S1808) was spin-coated on the Ni/glass substrate at 2500 rpm for 80 s, and the substrates was baked at 90° C. for 30 min. Then, the photoresist layer was patterned by using a photolithographic mask and UV light exposure (Newport model 97436, i-line, 365 nm, 500 W, and 2.5 sec). After then, the substrate was immersed in the developer solution (Shipley MF-319) for 20 s, washed with deionized water, and dried in air. To produce a horizontal undercut between the photoresist and the glass substrate, the samples was etched by 0.8 M nitric acid for 5 min. The Pd NWs were synthesized by the electrodeposition using a potentiostat (Gamry Instrument, model G300). The lithographically patterned glass substrate was immersed in aqueous plating solution containing 0.2 mM PdCl$_2$, 0.22 mM EDTA, and 0.1 M KCl (adjusted pH=4.9). The edge of Ni out of the plating solution was connected to the working electrode. The counter electrode was a platinum foil, and the reference electrode was saturated calomel electrode (SCE). The Pd NWs were electrodeposited at negative 0.80 V vs SCE. After electrodeposition, the substrate was rinsed with acetone to remove the photoresist layer. Then, the Ni layer was etched by 0.8 M nitric acid.

Synthesis of ZIF-8 coated Pd NWs. A Pd NW patterned glass substrate was placed in the bottom of the beaker. 0.293 g of Zn(NO$_3$)$_2$·6H$_2$O (0.293 g) and 0.649 g of mIM as precursor materials for the growth of ZiF-8 were dissolved in 30 mL of MeOH. Then, the solution was gently poured in the beaker. The coating thickness of ZIF-8 grown on Pd NWs was controlled by changing assembly time (2 h, 4 h, and 6 h) of ZIF-8 at RT. After assembly process, the substrate was washed by the EtOH by 5 times and dried overnight at RT.

Characterization. SEM (Magellan 400 XHR system, FEI) analysis was conducted to analyze the microstructures and morphologies of samples. EDS images were obtained by using same SEM equipment with an EDS detector (80 mm$^2$, Aztec software, Oxford Instruments). Atomic force microscopy (AFM, MFP-3D, Asylum Research) analysis was carried out to investigate the surface morphology of pristine Pd NWs and ZiF-8 coated Pd NWs. GIXRD (Ultima III, Rigaku) analysis with Cu Kα radiation (λ=1.5418 Å) was conducted to investigate the crystal structure.

Sensor fabrication and gas sensing measurement. The hydrogen sensors were prepared by evaporating Au electrodes of 60 nm thickness between NWs. The parallel Au electrodes were patterned between the Pd NWs (20 Ωm) on the Pd NWs patterned glass substrate. The resistance of samples was measured by using a four-probe system with a source meter (Model 2400, Keithley Instruments) and a digital multimeter (Model 2000, Keithley Instruments). The sensor was placed in a sealed chamber. Hydrogen (0.01 to 1%) and pure air were injected in the chamber for sensing measurement. To modulate the concentration of hydrogen, controlled the mass flow controllers (Model 1479A, MKS Inc.) were controlled using Labview (BNC 2110, National Instruments). All hydrogen sensing measurements were conducted at ambient temperature (RT, ~20° C.).

Embodiments of the present disclosure provide Pd NWs encapsulated by ZIF-8 layer synthesized by LPNE and subsequent assembly coated with ZIF-8 in methanol solution.

Embodiments of the present disclosure are directed to a bi-layer nanowire based hydrogen sensor. In embodiments, the bi-layer nanowire based hydrogen sensor comprises a plurality of nanowires, and a metal-organic framework (MOF) assembled on the plurality of nanowires.

In embodiments, the plurality of nanowires are palladium (PD).

In embodiments, the plurality of nanowires are lithographically patterned.

In embodiments, the MOF forms a protective hydrogen filter layer.

In embodiments, the MOF comprises a plurality of polyhedron particles of Zn based zeolite imidazole framework (ZIF-8).

In embodiments, the plurality of nanowires are patterned onto a glass substrate.

In embodiments, the MOF is assembled on the plurality of nanowires and the glass substrate.

In embodiments, the sensor has a response time in a range of 7 seconds to 13 seconds to 1% of $H_2$. In embodiments, the sensor has a recovery time in a range of 8 seconds to 15 seconds to 1% of $H_2$.

In embodiments, the sensor has an assembly time of 2 hours and a height of 160±20 nm.

In embodiments, the sensor has an assembly time of 4 hours and a height of 130±15 nm.

In embodiments, the sensor has an assembly time of 6 hours and a height of 35±10 nm.

Embodiments of the present disclosure are directed to a method for forming a bi-layer nanowire based hydrogen sensor, comprising the steps of patterning a plurality of palladium nanowires on a substrate, and immersing the substrate patterned with the plurality of palladium nanowires in a methanol (MeOH) solution including Zn precursors (Zn(NO$_3$)$_2$·6H$_2$O) and 2-methylimidazole (mIM), wherein ZIF-8 is assembled on both the plurality of palladium nanowires and the substrate by heterogeneous nucleation.

In embodiments, the assembly time for forming the bi-layer nanowire based hydrogen substrate is one of 2 hours, 4 hours, or 6 hours.

In embodiments, patterning the plurality of palladium nanowires comprises depositing a thin layer of nickel (Ni) on the substrate using a metal evaporator, spin-coating a photo-resist layer (PR) onto the thin layer of nickel (Ni), fabricating a horizontal trench by etching exposed Ni in a nitric acid, electro-depositing the plurality of palladium nanowires into the trench, and removing residual photo-resist (PR) and nickel (Ni) using acetone and nitric acid, respectively.

In embodiments, the substrate is glass. In embodiments, the bi-layer nanowire sensor has a response time in a range of 7 seconds to 13 seconds to 1% of $H_2$. In embodiments, the bi-layer nanowire sensor has a recovery time in a range of 8 seconds to 15 seconds to 1% of $H_2$. In embodiments, the bi-layer nanowire sensor has a height of 160±20 nm. In embodiments, the bi-layer nanowire sensor has a height of 130±15 nm. In embodiments, the bi-layer nanowire sensor has a height of 35±10 nm.

These examples are illustrative of the various embodiments and additional features that are afforded by the nanowire based sensor, and are not intended to represent an exhaustive list of features. The example embodiments provided herein, however, are merely intended as illustrative examples and not to be limiting in any way.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

In many instances, entities are described herein as being coupled to other entities. It should be understood that the terms "coupled" and "connected" (or any of their forms are used interchangeably herein and, in both cases, are generic to the direct coupling of two entities (without any non-negligible (e.g., parasitic intervening entities and the indirect coupling of two entities (with one or more non-negligible intervening entities. Where entities are shown as being directly coupled together, or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed:

1. A bi-layer nanowire based hydrogen sensor, comprising:
   a plurality of palladium nanowires patterned onto a glass substrate, and
   a metal-organic framework (MOF) assembled on the plurality of nanowires, wherein a plurality of polyhedron particles of Zn based zeolite imidazole framework (ZIF-8) are deposited on the glass substrate and the surface of the palladium nanowires, wherein the plurality of polyhedron particles of Zn based zeolite imidazole framework (ZIF-8) are deposited directly on the glass substrate and the nanowires.

2. The sensor of claim 1, wherein the plurality of nanowires are lithographically patterned.

3. The sensor of claim 1, wherein the MOF forms a protective hydrogen filter layer.

4. The sensor of claim 1, having a response time in a range of 7 seconds to 13 seconds to 1% of $H_2$.

5. The sensor of claim 1, having a recovery time in a range of 8 seconds to 15 seconds to 1% of $H_2$.

6. The sensor of claim 1, having an assembly time of 2 hours and a height of 160±20 nm.

7. The sensor of claim 1, having an assembly time of 4 hours and a height of 130±15 nm.

8. The sensor of claim 5, having an assembly time of 6 hours and a height of 35±10 nm.

* * * * *